US012105842B1

(12) United States Patent
Dods et al.

(10) Patent No.: US 12,105,842 B1
(45) Date of Patent: Oct. 1, 2024

(54) VERIFIABLE CREDENTIALLING AND MESSAGE CONTENT PROVENANCE AUTHENTICATION

(71) Applicant: LEDGERDOMAIN INC., Las Vegas, NV (US)

(72) Inventors: Victor Bovee Dods, Seattle, WA (US); Leonid Alekseyev, San Francisco, CA (US); Alex Read Colgan, Yarmouth (CA); Benjamin James Taylor, Las Vegas, NV (US); William Jack, Boston, MA (US); Benjamin Gregory Nichols, New Plymouth (NZ)

(73) Assignee: LEDGERDOMAIN INC., Las Vegas, NV (US)

( * ) Notice: Subject to any disclaimer, the term of this patent is extended or adjusted under 35 U.S.C. 154(b) by 0 days.

(21) Appl. No.: 18/234,293

(22) Filed: Aug. 15, 2023

Related U.S. Application Data

(63) Continuation-in-part of application No. 17/492,488, filed on Oct. 1, 2021, now Pat. No. 11,769,577, which
(Continued)

(51) Int. Cl.
*G06F 21/62* (2013.01)
*G06F 17/18* (2006.01)
(Continued)

(52) U.S. Cl.
CPC .......... *G06F 21/6245* (2013.01); *G06F 17/18* (2013.01); *G06F 18/22* (2023.01);
(Continued)

(58) Field of Classification Search
CPC ...... G06F 21/6245; G06F 17/18; G06F 18/22; G06F 18/23; G06F 21/6227; G06N 3/08;
(Continued)

(56) References Cited

U.S. PATENT DOCUMENTS

| 7,170,391 | B2 | 1/2007 | Lane et al. |
| 9,870,508 | B1 | 1/2018 | Hodgson et al. |

(Continued)

FOREIGN PATENT DOCUMENTS

| CN | 110597902 A | 12/2019 |
| WO | 2018206408 A1 | 11/2018 |

(Continued)

OTHER PUBLICATIONS

U.S. Appl. No. 17/063,585, filed Oct. 5, 2020, U.S. Pat. No. 11,245,691, Feb. 8, 2022, Granted.
(Continued)

*Primary Examiner* — Taghi T Arani
*Assistant Examiner* — Blake I Narramore
(74) *Attorney, Agent, or Firm* — Haynes Beffel & Wolfeld LLP; Andrew L. Dunlap; Paul A. Durdik

(57) ABSTRACT

The technology disclosed allows for leveraging decentralized credentials to achieve bidirectional authentication between two actors leveraging a messaging platform/system, such as email or another text-based system, verifiable credentials (VCs), and secure web endpoints. It empowers one party ("Sender") to send a message enclosed with a Verifiable Presentation which allows another party ("Recipient") to authenticate the message's provenance and the identity of the sender. Moreover, the message contains a link to a secure web endpoint, where the recipient can submit a response signed by their own Verifiable Presentation, allowing the Sender to authenticate the identity of the Recipient. In this way, both participants are able to authenticate each other's identities with an additional factor of authentication, with neither participant being required to share a single service.

21 Claims, 20 Drawing Sheets

Verifiable Credentialling and Message Content Provenance Authentication System 100

Related U.S. Application Data is a continuation-in-part of application No. 17/384,585, filed on Jul. 23, 2021, now Pat. No. 11,829,510, which is a continuation of application No. 17/063,605, filed on Oct. 5, 2020, now Pat. No. 11,081,219.

(60) Provisional application No. 63/398,455, filed on Aug. 16, 2022, provisional application No. 63/122,875, filed on Dec. 8, 2020, provisional application No. 62/961,594, filed on Jan. 15, 2020.

(51) Int. Cl.
*G06F 18/22* (2023.01)
*G06F 18/23* (2023.01)
*G06N 3/08* (2023.01)
*G06N 20/00* (2019.01)
*G16H 20/10* (2018.01)
*H04L 9/00* (2022.01)
*H04L 9/06* (2006.01)
*H04L 9/40* (2022.01)

(52) U.S. Cl.
CPC .......... *G06F 18/23* (2023.01); *G06F 21/6227* (2013.01); *G06N 3/08* (2013.01); *G06N 20/00* (2019.01); *G16H 20/10* (2018.01); *H04L 9/0643* (2013.01); *H04L 63/0838* (2013.01); *H04L 63/0853* (2013.01); *H04L 63/108* (2013.01); *H04L 9/50* (2022.05)

(58) Field of Classification Search
CPC ...... G06N 20/00; G16H 20/10; H04L 9/0643; H04L 63/0838; H04L 63/0853; H04L 63/108; H04L 9/50
See application file for complete search history.

(56) References Cited

U.S. PATENT DOCUMENTS

| | | | |
|---|---|---|---|
| 10,268,974 B2 | 4/2019 | Wiig et al. | |
| 10,356,087 B1* | 7/2019 | Vetter | G06F 21/36 |
| 10,491,404 B1 | 11/2019 | Yamamoto | |
| 10,491,578 B1 | 11/2019 | Hebert et al. | |
| 10,496,802 B2 | 12/2019 | Weis | |
| 10,509,684 B2 | 12/2019 | Florissi et al. | |
| 10,516,525 B2 | 12/2019 | Bhattacharya et al. | |
| 10,540,704 B2 | 1/2020 | Mazed et al. | |
| 10,542,046 B2 | 1/2020 | Katragadda et al. | |
| 10,990,693 B1 | 4/2021 | Newman | |
| 11,468,046 B2 | 10/2022 | Conley et al. | |
| 11,509,709 B1 | 11/2022 | Basak et al. | |
| 11,736,290 B1 | 8/2023 | Dods et al. | |
| 11,741,215 B1 | 8/2023 | Dods et al. | |
| 11,741,216 B1 | 8/2023 | Dods et al. | |
| 11,769,577 B1 | 9/2023 | Dods et al. | |
| 11,829,510 B2 | 11/2023 | Dods et al. | |
| 11,848,754 B1 | 12/2023 | Dods et al. | |
| 2012/0130905 A1 | 5/2012 | Tsudik et al. | |
| 2014/0006048 A1 | 1/2014 | Liberty | |
| 2014/0025443 A1 | 1/2014 | Onischuk | |
| 2014/0040153 A1* | 2/2014 | Singh | G06Q 30/02 705/320 |
| 2014/0108043 A1* | 4/2014 | Ach | G16H 10/60 705/3 |
| 2015/0039700 A1* | 2/2015 | West | G06Q 10/107 709/206 |
| 2015/0262171 A1 | 9/2015 | Langschaedel et al. | |
| 2015/0269379 A1 | 9/2015 | Ramzan et al. | |
| 2016/0125199 A1 | 5/2016 | Lee et al. | |
| 2016/0155069 A1 | 6/2016 | Hoover et al. | |
| 2016/0212146 A1 | 7/2016 | Wilson | |
| 2017/0103167 A1 | 4/2017 | Shah | |
| 2017/0221032 A1 | 8/2017 | Mazed | |
| 2017/0286880 A1 | 10/2017 | Wiig et al. | |
| 2017/0310653 A1 | 10/2017 | Zhang | |
| 2017/0337588 A1* | 11/2017 | Chittilappilly | G06Q 30/0244 |
| 2018/0048461 A1* | 2/2018 | Jutla | H04L 9/3268 |
| 2018/0114169 A1 | 4/2018 | Wiig et al. | |
| 2018/0139186 A1 | 5/2018 | Castagna | |
| 2018/0341648 A1* | 11/2018 | Kakavand | G06F 16/1873 |
| 2019/0012249 A1 | 1/2019 | Mercuri et al. | |
| 2019/0020661 A1 | 1/2019 | Zhang | |
| 2019/0026450 A1 | 1/2019 | Egner et al. | |
| 2019/0051079 A1 | 2/2019 | Venkataraman et al. | |
| 2019/0052453 A1* | 2/2019 | de Ligt | H04L 9/321 |
| 2019/0057386 A1 | 2/2019 | Fazeli et al. | |
| 2019/0058599 A1 | 2/2019 | Takada Chino et al. | |
| 2019/0068562 A1 | 2/2019 | Iyer et al. | |
| 2019/0075102 A1 | 3/2019 | Kim et al. | |
| 2019/0108898 A1 | 4/2019 | Gulati | |
| 2019/0138905 A1 | 5/2019 | Akella et al. | |
| 2019/0138971 A1 | 5/2019 | Uggirala et al. | |
| 2019/0141119 A1* | 5/2019 | Bernat | H04L 41/12 |
| 2019/0171438 A1 | 6/2019 | Franchitti | |
| 2019/0180276 A1 | 6/2019 | Lee et al. | |
| 2019/0222570 A1* | 7/2019 | Krishan | G06F 21/45 |
| 2019/0228174 A1 | 7/2019 | Withrow et al. | |
| 2019/0251295 A1 | 8/2019 | Vieyra | |
| 2019/0281066 A1 | 9/2019 | Simons | |
| 2019/0325507 A1 | 10/2019 | Rowley et al. | |
| 2019/0333116 A1 | 10/2019 | Bhardwaj et al. | |
| 2019/0334716 A1 | 10/2019 | Kocsis et al. | |
| 2019/0392162 A1 | 12/2019 | Stern et al. | |
| 2020/0005133 A1 | 1/2020 | Zhang et al. | |
| 2020/0013229 A1 | 1/2020 | Lee et al. | |
| 2020/0019288 A1 | 1/2020 | D'Amore et al. | |
| 2020/0084483 A1 | 3/2020 | Brown et al. | |
| 2020/0110821 A1 | 4/2020 | Chan et al. | |
| 2020/0118060 A1 | 4/2020 | Mukherjee et al. | |
| 2020/0137557 A1* | 4/2020 | Touati | H04W 88/04 |
| 2020/0153606 A1 | 5/2020 | Li et al. | |
| 2020/0186358 A1 | 6/2020 | Capola et al. | |
| 2020/0213218 A1* | 7/2020 | Demeilliez | H04W 40/24 |
| 2020/0219099 A1* | 7/2020 | Mohassel | G06Q 20/223 |
| 2020/0252205 A1 | 8/2020 | Padmanabhan | |
| 2020/0258166 A1 | 8/2020 | Cross et al. | |
| 2020/0265031 A1* | 8/2020 | Greven | H04L 67/1097 |
| 2020/0268260 A1 | 8/2020 | Tran | |
| 2020/0294033 A1 | 9/2020 | Wilson et al. | |
| 2020/0320207 A1 | 10/2020 | Beno et al. | |
| 2020/0322169 A1 | 10/2020 | Michaud et al. | |
| 2020/0374137 A1 | 11/2020 | Godfrey | |
| 2020/0374145 A1* | 11/2020 | Kau | H04L 12/1831 |
| 2020/0389499 A1* | 12/2020 | Koval | H04L 63/0823 |
| 2020/0403809 A1 | 12/2020 | Chan et al. | |
| 2021/0034779 A1 | 2/2021 | Signorini et al. | |
| 2021/0126797 A1 | 4/2021 | Peng | |
| 2021/0136068 A1 | 5/2021 | Smeets et al. | |
| 2021/0150205 A1 | 5/2021 | Snyder et al. | |
| 2021/0158309 A1* | 5/2021 | McGinlay | G06N 3/02 |
| 2021/0174914 A1 | 6/2021 | Cano et al. | |
| 2021/0182539 A1 | 6/2021 | Rassool | |
| 2021/0208960 A1 | 7/2021 | Dande et al. | |
| 2021/0218720 A1 | 7/2021 | Oberhauser et al. | |
| 2021/0234672 A1 | 7/2021 | Zeng et al. | |
| 2021/0264520 A1 | 8/2021 | Cummings | |
| 2022/0051240 A1 | 2/2022 | Shamai et al. | |
| 2022/0051314 A1 | 2/2022 | Enkhtaivan | |
| 2022/0052988 A1 | 2/2022 | Gadnis et al. | |
| 2022/0083936 A1 | 3/2022 | Balinsky et al. | |
| 2022/0150077 A1 | 5/2022 | Kim | |
| 2022/0179378 A1 | 6/2022 | Gourisetti et al. | |
| 2022/0405750 A1 | 12/2022 | Fallah et al. | |
| 2022/0407856 A1 | 12/2022 | Jawed | |
| 2022/0414237 A1 | 12/2022 | Lally et al. | |
| 2022/0417331 A1 | 12/2022 | Devine et al. | |
| 2023/0006845 A1 | 1/2023 | Leedom, Jr. | |

FOREIGN PATENT DOCUMENTS

| | | |
|---|---|---|
| WO | 2019086553 A1 | 5/2019 |
| WO | 2019090264 A1 | 5/2019 |
| WO | 2019090268 A1 | 5/2019 |

(56) References Cited

FOREIGN PATENT DOCUMENTS

| WO | 2019207297 A1 | 10/2019 |
|---|---|---|
| WO | 2020006121 A1 | 1/2020 |
| WO | 2021127577 A1 | 6/2021 |

OTHER PUBLICATIONS

U.S. Appl. No. 17/063,605, filed Oct. 5, 2020, U.S. Pat. No. 11,081,219, Aug. 3, 2021, Granted.
U.S. Appl. No. 17/384,585, filed Jul. 23, 2021, 20210350891, Nov. 11, 2021, Allowed.
U.S. Appl. No. 17/665,471, filed Feb. 4, 2022, Allowed.
U.S. Appl. No. 17/492,488, filed Oct. 1, 2021, U.S. Pat. No. 11,769,577, Sep. 26, 2023, Granted.
U.S. Appl. No. 18/372,029, filed Sep. 22, 2023, Pending.
U.S. Appl. No. 18/372,037, filed Sep. 22, 2023, Pending.
Newton, The battle inside Signal, The Verge, dated Jan. 25, 2021, 19 pages. Retrieved on Oct. 3, 2021. Retrieved from the internet. [URL: https://www.theverge.com/platform/amp/22249391/signal-app-abuse-messaging-employees-violence-misinformation ].
Tobin et al., The Inevitable Rise of Self-Sovereign Identity, Sovrin Foundation Whitepaper, updated Mar. 28, 2017, 24 pages. Retrieved on Oct. 3, 2021. Retrieved from the internet [URL: https://sovrin.org/wp-content/uploads/2018/03/The-Inevitable-Rise-of-Self-Sovereign-Identity.pdf ].
Mitre, Broad Coalition of Health and Technology Industry Leaders Announce Vaccination Credential Initiative to Accelerate Digital Access to COVID-19 Vaccination Records, dated Jan. 14, 2021, 5 pages. Retrieved on Oct. 3, 2021. Retrieved from the internet [URL: https://www.businesswire.com/news/home/20210114005294/en/Broad-Coalition-of-Health-and-Technology-Industry-Leaders-Announce-Vaccination-Credential-Initiative-to-Accelerate-Digital-Access-to-COVID-19-Vaccination-Records ].
The Commons project, Unlocking the full potential of technology and data for the common good, 2019-2021, 5 pages. Retrieved on Oct. 3, 2021. Retrieved from the internet [URL: https://thecommonsproject.org/commonpass ].
What are SMART Health Cards?, SMART Health Cards Framework, 2021, 4 pages. Retrieved on Oct. 3, 2021. Retrieved from the internet [URL: https://smarthealth.cards/ ].
HDA Saleable Returns Pilot Study Identifies Two Recommendations to Meet 2019 DSCSA Requirements, Healthcare Distribution Alliance (HDA), dated Nov. 10, 2016, 5 pages. Retrieved on Oct. 3, 2021. Retrieved from the internet [URL: https://www.hda.org/news/2016-11-10-hda-pilot-results-revealed ].
FDA's Technology Modernization Action Plan (TMAP), Food and Drug Administration (FDA), dated Sep. 18, 2019, 10 pages. Retrieved on Oct. 3, 2021. Retrieved from the internet [URL: https://www.fda.gov/media/130883/download].
GS1 Standards Resources for DSCSA Implementation Support, GS1 US, dated Feb. 22, 2021, 7 pages. Retrieved on Oct. 3, 2021. Retrieved from the internet [URL: https://www.gs1us.org/industries/healthcare/standards-in-use/pharmaceutical/dscsa-resources ].
Reed et al., Decentralized Identifiers: The linchpin of SSI, What are Decentralized Identifiers (DIDs)?, Evernym on Slideshare, dated Sep. 30, 2019, 29 pages. Retrieved on Oct. 3, 2021. Retrieved from the internet [URL: https://www.slideshare.net/Evernym/what-are-decentralized-identifiers-dids ].
Object Management Group Issues Request for Information for Disposable Self-Sovereign Identity Standard, Object Management Group (OMG), dated Jan. 21, 2021, 3 pages. Retrieved on Oct. 3, 2021. Retrieved from the internet [URL: https://www.omg.org/news/releases/pr2021/Jan. 21, 21.htm ].
Lodder et al., Sovrin DID Method Specification, Sovrin Foundation, dated Aug. 20, 2021, 16 pages. Retrieved on Oct. 3, 2021. Retrieved from the internet [URL: https://sovrin-foundation.github.io/sovrin/spec/did-method-spec-template.html ].
Looker et al., BBS+ Signatures 2020 Draft Community Group Report, W3C Community Group, dated Jun. 13, 2021, 31 pages. Retrieved on Oct. 3, 2021. Retrieved from the internet [URL: https://w3c-ccg.github.io/ldp-bbs2020/ ].
Hyperledger, Ursa, Github, updated 2021, 7 pages. Retrieved on Oct. 3, 2021. Retrieved from the internet [URL: https://github.com/hyperledger/ursa ].
Partnership for DSCSA Governance, PDG, 2021, 3 pages. Retrieved on Oct. 3, 2021. Retrieved from the internet [URL: https://dscsagovernance.org/ ].
Thayer, "Why Does Mozilla Maintain Our Own Root Certificate Store?", Mozilla Security Blog, dated Feb. 14, 2019, 3 pages. Retrieved on Oct. 3, 2021. Retrieved from the internet [URL: https://blog.mozilla.org/security/2019/02/14/why-does-mozilla-maintain-our-own-root-certificate-store/ ].
Otto et al., Verifiable Credentials Use Cases, W3C Working Group, dated Sep. 24, 2019, 35 pages. Retrieved on Oct. 3, 2021. Retrieved from the internet [URL: https://www.w3.org/TR/vc-use-cases/ ].
Entities, Spherity, 3 pages. Retrieved on Oct. 3, 2021. Retrieved from the internet [URL: https://docs.spherity.com/spherity-api/verifiable-credentials-api/entities ].
General Meeting Agenda—Healthcare SIG, Hyperledger Foundation, updated Feb. 17, 2021, 2 pages. Retrieved on Oct. 3, 2021. Retrieved from the internet [URL: https://wiki.hyperledger.org/display/HCSIG/2021.02.17+General+Meeting+Agenda ].
Google Protocol Buffers—Google's data interchange format, Github, dated 2008, 6 pages. Retrieved on Oct. 3, 2021. Retrieved from the internet [URL: https://github.com/protocolbuffers/protobuf ].
Dodds, Follow Your Nose, Linked Data Patterns, dated May 31, 2012, 2 pages. Retrieved on Oct. 3, 2021. Retrieved from the internet [URL: https://patterns.dataincubator.org/book/follow-your-nose.html ].
Searls, New Hope for Digital Identity, Linux Journal, dated Nov. 9, 2017, 7 pages. Retrieved on Oct. 4, 2021. Retrieved from the internet [URL: https://www.linuxjournal.com/content/new-hope-digital-identity ].
Web Assembly, Mozilla Developer Network (MDN), dated 2021, 31 pages. Retrieved on Oct. 5, 2021. Retrieved from the internet [URL: https://developer.mozilla.org/en-US/docs/WebAssembly ].
Rossberg, WebAssembly Core Specification, W3C Working Group, W3C, dated Dec. 5, 2019, 164 pages. Retrieved on Oct. 5, 2021. Retrieved from the internet [URL: https://www.w3.org/TR/wasm-core-1/].
Kaptijn et al., X.509 Did method, WebOfTrustInfo, GitHub, dated Aug. 12, 2019, 6 pages. Retrieved on Oct. 5, 2021. Retrieved from the internet [URL: https://github.com/WebOfTrustInfo/rwot9-prague/blob/master/topics-and-advance-readings/X.509-DID-Method.md ].
Sovrin Governance Framework Working Group, Sovrin Governance Framework V2, Sovrin Foundation, dated Dec. 4, 2019, 20 pages. Retrieved on Oct. 5, 2021. Retrieved from the internet [URL: https://sovrin.org/wp-content/uploads/Sovrin-Governance-Framework-V2-Master-Document-V2.pdf ].
Callahan et al., Six Principles for Self-Sovereign Biometrics, Web of Trust Info., GitHub, dated Oct. 6, 2019, 7 pages. Retrieved on Oct. 5, 2021. Retrieved from the internet [URL: https://github.com/WebOfTrustInfo/rwot6-santabarbara/blob/master/draft-documents/Biometrics.md].
Identity-concept.svg, Wikimedia Commons, 3 pages. Retrieved on Oct. 6, 2021. Retrieved from the internet [URL: https://commons.wikimedia.org/wiki/File:Identity-concept.svg ].
Hardman, Verifiable Data Registry (Image), Wikipedia, dated Nov. 5, 2019, 1 page. Retrieved on Oct. 6, 2021. Retrieved from the internet [URL: https://en.wikipedia.org/wiki/Verifiable_credentials#/media/File:VC_triangle_of_Trust.svg ].
Untitled code sample, W3C Working Group, W3C, dated 2018, 7 pages. Retrieved on Oct. 6, 2021. Retrieved from the internet [URL: https://www.w3.org/2018/credentials/v1 ].
DIF—Decentralized Identity Foundation, Homepage, dated 2021, 8 pages. Retrieved on Oct. 6, 2021. Retrieved from the internet [URL: https://identity.foundation/ ].
How to share an OpenPGP public key easily in three steps, Mailfence, dated Jul. 11, 2017, 14 pages. Retrieved on Aug. 13, 2021. Retrieved from the internet [URL: https://blog.mailfence.com/openpgp-public-key/ ].

(56) References Cited

OTHER PUBLICATIONS

Abid et al., Block-Chain Security Advancement in Medical Sector for sharing Medical Records, 2019 International Conference on Innovative Computing (ICIC) (Year: 2019).
Rahman et al., Blockchain Based Mobile Edge Computing Framework for Secure Therapy Applications, 2018, IEEE Special Section on Mobile Multimedia for Healthcare, vol. 6, pp. 72469-72478 (Year: 2018).
U.S. Food and Drug Administration, Drug Supply Chain Security Act Law and Policies, U.S. Department of Health and Human Services Food and Drug Administration, updated Oct. 23, 2020, 6 pages. Retrieved on Oct. 1, 2021. Retrieved from the internet [URL: https://www.fda.gov/drugs/drug-supply-chain-security-act-dscsa/drug-supply-chain-security-act-law-and-policies].
GS1 Healthcare U.S., GS1 Lightweight Messaging Standard for Verification of Product Identifiers, dated Dec. 2018, 30 pages. Retrieved on Oct. 2, 2021. Retrieved from the internet [URL: https://www.gs1.org/docs/epc/GS1_Lightweight_Verification_Messaging_Standard.pdf ].
U.S. Department of Health and Human Services Food and Drug Administration, Wholesale Distributor Verification Requirement for Saleable Returned Drug Product and Dispenser Verification Requirements When Investigating a Suspect or Illegitimate Product—Compliance Policies, Guidance for Industry, dated Oct. 2020, 10 pages. Retrieved on Oct. 2, 2021. Retrieved from the internet [URL: https://www.fda.gov/media/131005/download ].
Shuaib et al., Blockchains for Secure Digitized Medicine, Journal of Personalized Medicine, dated Jul. 13, 2019, 9(3):35, 21 pages. Retrieved on Oct. 2, 2021. Retrieved from the internet [URL: https://www.mdpi.com/2075-4426/9/3/35 ].
Brook, "What's the Cost of a Data Breach in 2019?", Data Insider—Digital Guardian, dated Dec. 1, 2020, 8 pages. Retrieved on Oct. 2, 2021. Retrieved from the internet [URL: https://digitalguardian.com/blog/whats-cost-data-breach-2019 ].
Keen et al., Gartner Forecasts Worldwide Information Security Spending to Exceed $124 Billion in 2019, Gartner, dated Aug. 15, 2018, 5 pages. Retrieved on Oct. 2, 2021. Retrieved from the internet [URL: https://www.gartner.com/en/newsroom/press-releases/2018-08-15-gartner-forecasts-worldwide-information-security-spending-to-exceed-124-billion-in-2019 ].
Bourque, Ditching passwords and increasing e-commerce conversion rates by 54%, CIO, dated May 1, 2017, 4 pages. Retrieved on Oct. 2, 2021. Retrieved from the internet [URL: https://www.cio.com/article/3193206/ditching-passwords-and-increasing-ecommerce-conversion-rates-by-54.html ].
Bossert, I Was the Homeland Security Adviser to Trump. We're Being Hacked., The New York Times, dated Dec. 16, 2020, 3 pages. Retrieved on Oct. 3, 2021. Retrieved from the internet [URL: https://www.nytimes.com/2020/12/16/opinion/fireeye-solarwinds-russia-hack.html ].
U.S. Department of Health and Human Services, Food and Drug Administration, Identifying Trading Partners Under the Drug Supply Chain Security Act, Guidance for Industry, dated Aug. 2017, 18 pages. Retrieved on Oct. 3, 2021. Retrieved from the internet [URL: https://www.fda.gov/files/drugs/published/Identifying-Trading-Partners-Under-the-Drug-Supply-Chain-Security-Act-Guidance-for-Industry.pdf ].
Ashkar et al., Evaluation of Decentralized Verifiable Credentials to Authenticate Authorized Trading Partners and Verify Drug Provenance, Blockchain for Healthcare Today, dated Mar. 11, 2021, 14 pages. Retrieved on Oct. 3, 2021. Retrieved from the internet [URL: https://blockchainhealthcaretoday.com/index.php/journal/article/view/168 ].
Sporny et al., Verifiable Credentials Data Model 1.0, W3C Working Group. dated Nov. 19, 2019, 122 pages. Retrieved on Oct. 3, 2021. Retrieved from the internet [URL: https://www.w3.org/TR/vc-data-model/ ].
Housley et al., Trust Anchor Format, Internet Engineering Task Force (IETF), dated Jun. 2021, 14 pages. Retrieved on Oct. 3, 2021. Retrieved from the internet [URL: https://datatracker.ietf.org/doc/html/rfc5914 ].
Young, Verifiable Credentials Flavors Explained, COVID-19 Credentials Initiative, dated Feb. 2021, 21 pages. Retrieved on Oct. 3, 2021. Retrieved from the internet [URL: https://www.lfph.io/wp-content/uploads/2021/02/Verifiable-Credentials-Flavors-Explained.pdf ].
Temoshok et al., Developing Trust Frameworks to Support Identity Federations, National Institute of Standards and Technology (NIST), dated Jan. 2018, 34 pages. Retrieved on Oct. 4, 2021. Retrieved from the internet [URL: http://dx.doi.org/10.6028/NIST.IR.8149 ].
Makaay et al., Frameworks for Identity Systems, Open Identity Exchange (OIX), dated Jun. 2017, 18 pages. Retrieved on Oct. 5, 2021. Retrieved from the internet [URL: https://connectis.com/wp-content/uploads/2018/05/OIX-White-Paper_Trust-Frameworks-for-Identity-Systems_Final.pdf].
Rose et al., Zero Trust Architecture, NIST Special Publication 800-207, dated Aug. 2020, 59 pages. Retrieved on Oct. 6, 2021. Retrieved from the internet [URL: https://csrc.nist.gov/publications/detail/sp/800-207/final ].
Bogdanov, Pseudorandom Functions: Three Decades Later, dated 2017, 72 pages. Retrieved on Oct. 6, 2021. Retrieved from the internet [URL: https://eprint.iacr.org/2017/652.pdf].
Grassi et al., Digital Identity Guidelines, NIST Special Publication 800-63-3, dated Jun. 2017, 75 pages. Retrieved on Oct. 6, 2021. Retrieved from the internet [URL: https://doi.org/10.6028/NIST.SP.800-63-3.
Grassi et al., Digital Identity Guidelines: Authentication and Lifecycle Management, NIST Special Publication 800-63B, dated Jun. 2017, 79 pages. Retrieved on Oct. 6, 2021. Retrieved from the internet [URL: https://doi.org/10.6028/NIST.SP.800-63b ].
Pharmacompass, Top 1000 Global Pharmaceutical Companies, LePro PharmaCompass OPC, dated Sep. 2020, 101 pages. Retrieved on Oct. 6, 2021. Retrieved from the internet [URL: https://www.pharmacompass.com/data-compilation/top-1000-global-pharmaceutical-companies ].
Hammi, M.T. et al., Apr. 2018. "BCTrust: A decentralized authentication blockchain-based mechanism". In 2018 IEEE wireless communications and networking conference (WCNC) (pp. 1-6). IEEE. (Year: 2018), in 6 pages.
Prabha, P. et al., Dec. 2020. Securing telecare medical information system with blockchain technology. In 2020 2nd International Conference on Advances in Computing, Communication Control and Networking (ICACCCN) (pp. 846-851). IEEE. (Year: 2020), in 6 pages.
Grassi et. al., Digital Identity Guidelines: Federation and Assertions, NIST Special Publication 800-63C, dated Jun. 2017, 49 pages. Retrieved on Oct. 6, 2021. Retrieved from the internet [URL: https://doi.org/10.6028/NIST.SP.800-63c ].
Grassi et al., NIST Special Publication 800-63C, Digital Identity Guidelines—Federation and Assertions, retrieved on Oct. 1, 2021, 48 pages. Retrieved from [ URL: https://pages.nist.gov/800-63-3/sp800-63c.html ].
GS1 Healthcare U.S. Standard 1.1—Applying the GS1 Lightweight Messaging Standard for DSCSA Verification of Returned Product Identifiers, dated Mar. 31, 2020, 60 pages. Retrieved on Oct. 1, 2021. Retrieved from the Internet [URL: https://www.gs1us.org/DesktopModules/Bring2mind/DMX/Download.aspx?Command=Core_Download&EntryId=1897&language=en-US&PortalId=0&TabId=134 ].
GS1 Healthcare U.S., Assessing Current Implementation of DSCSA Serialization Requirements, GS1 US, dated 2018, 6 pages. Retrieved on Oct. 2, 2021. Retrieved from the internet [URL: https://www.gs1us.org/DesktopModules/Bring2mind/DMX/Download.aspx?Command=Core_Download&EntryId=1210&language=en-US&PortalId=0&TabId=134 ].
GS1 Healthcare U.S., Standard 1.2, Applying GS1 Standards for DSCSA and Traceability, dated Nov. 7, 2016, 126 pages. Retrieved on Oct. 2, 2021. Retrieved from the internet [URL: https://www.

(56) References Cited

OTHER PUBLICATIONS gs1us.org/DesktopModules/Bring2mind/DMX/Download.aspx?Command=Core_Download&EntryId=749&language=en-US&PortalId=0&TabId=134 ].

Drug Supply Chain Security Act (DSCSA), Food and Drug Administration (FDA), retrieved on Oct. 1, 2021, 3 pages. Retrieved from [URL: https://www.fda.gov/drugs/drug-supply-chain-integrity/drug-supply-chain-security-act-dscsa ].

Callahan, Council Post: Know Your Customer (KYC) Will Be a Great Thing When It Works, Forbes, dated Jul. 10, 2018, 8 pages. Retrieved on Oct. 1, 2021. Retrieved from [URL: https://www.forbes.com/sites/forbestechcouncil/2018/07/10/know-your-customer-kyc-will-be-a-great-thing-when-it-works/?sh=722a21178dbb ].

Freisleben, VRS Updates: Past, Present and Future, dated Dec. 12, 2018, Healthcare Distribution Alliance (HDA) 6 pages. Retrieved on Oct. 1, 2021. Retrieved from the internet [URL: https://www.hda.org/news/hda-blog/2018/12/07/14/44/2018-12-12-vrs-update-past-present-future ].

Jurgens, Industry-wide DSCSA Compliance Pilot Successfully Completed, Spherity, dated Dec. 17, 2020, 15 pages. Retrieved on Oct. 1, 2021. Retrieved from the internet [URL: https://medium.com/spherity/industry-wide-dscsa-compliance-pilot-successfully-completed-d7223a0f2c92 ].

XATP Working Group, Framework for extended ATP Authentication, Enhanced Verification and Saleable Returns Documentation, LedgerDomain, dated Dec. 17, 2020, 25 pages. Retrieved on Oct. 1, 2021. Retrieved from the internet [URL: https://www.xatp.org/publications ].

Chadwick et. al., Verifiable Credentials Data Model 1.0: Expressing verifiable information on the Web, World Wide Web Consortium (W3C), dated Nov. 19, 2019, 68 pages. Retrieved on Oct. 1, 2021. Retrieved from the internet [URL: https://www.w3.org/TR/vc-data-model/ ].

GS1 U.S., DSCSA Pilot Project readiness results, PDG FDA Pilot Program Round-Robin Webinar Series, dated Jun. 30, 2020, slides 16-29. Retrieved on Oct. 2, 2021. Retrieved from the internet [URL: : https://dscsagovernance.org/wp-content/uploads/2020/08/Attachment-A-Presentations.pdf ], in 15 pages.

U.S. Department of Health and Human Services Food and Drug Administration, Verification Systems Under the Frug Supply Chain Security Act for Certain Prescription Drugs, Guidance for Industry, Draft Guidance, dated Oct. 2018, 14 pages. Retrieved on Oct. 2, 2021. Retrieved from the internet [URL: https://www.fda.gov/media/117950/download ].

DSCSA Pilot Project Program, Food and Drug Administration (FDA), updated May 22, 2019, 4 pages. Retrieved on Oct. 2, 2021. Retrieved from the internet [URL: https://www.fda.gov/drugs/drug-supply-chain-security-act-dscsa/dscsa-pilot-project-program ].

Chien et al., The Last Mile: DSCSA Solution Through Blockchain Technology: Drug Tracking, Tracing and Verification at the Last Mile of the Pharmaceutical Supply Chain with BRUINchain, Blockchain in Healthcare Today, dated Mar. 12, 2020, 28 pages. Retrieved on Oct. 2, 2021. Retrieved from the internet [URL: https://blockchainhealthcaretoday.com/index.php/journal/article/view/134 ].

Androulaki et al., Hyperledger Fabric: A distributed operating system for permissioned blockchains, Proceedings for EuroSys 2018 Conference, revised Apr. 17, 2018, 15 pages. Retrieved on Oct. 2, 2021. Retrieved from the internet [URL: https://arxiv.org/abs/1801.10228 ].

Gabay, Federal Controlled Substances Act: Ordering and Recordkeeping, Hospital Pharmacy, dated Dec. 9, 2013, 3 pages. Retrieved on Oct. 2, 2021. Retrieved from the internet [URL: https://www.ncbi.nlm.nih.gov/pmc/articles/PMC3875106/].

Federal Trade Commission, Federal Law Requires All Businesses to Truncate Credit Card Information on Receipts, Federal Trade Commission (FTC), dated May 2007, 3 pages. Retrieved on Oct. 2, 2021. Retrieved from the internet [URL: https://www.ftc.gov/tips-advice/business-center/guidance/slip-showing-federal-law-requires-all-businesses-truncate ].

Matney, Apple's global active install base of iPhones surpassed 900 million this quarter, TechCrunch, dated Jan. 29, 2019, 2 pages. Retrieved on Oct. 2, 2021. Retrieved from the internet [URL: https://techcrunch.com/2019/01/29/apples-global-active-install-base-of-iphones-surpassed-900-million-this-quarter/].

Ponemon, What's New in the 2019 Cost of a Data Breach Report, Security Intelligence, dated Jul. 23, 2019, 10 pages. Retrieved on Oct. 2, 2021. Retrieved from the internet [URL: https://securityintelligence.com/posts/whats-new-in-the-2019-cost-of-a-data-breach-report/ ].

Steel, Passwords Are Still a Problem According to the 2019 Verizon Data Breach Investigations Report, LastPass Blog, dated May 21, 2019, 4 pages. Retrieved on Oct. 2, 2021. Retrieved from the internet [URL: https://blog.lastpass.com/2019/05/passwords-still-problem-according-2019-verizon-data-breach-investigations-report/ ].

Lu, "How Much are Password Resets Costing Your Company?", Okta, dated Aug. 20, 2019, 2 pages. Retrieved on Oct. 2, 2021. Retrieved from the internet [URL: https://www.okta.com/blog/2019/08/how-much-are-password-resets-costing-your-company/ ].

StClair et al., Blockchain, Interoperability, and Self-Sovereign Identity: Trust Me, It's My Data, Blockchain in Healthcare Today, dated Jan. 6, 2020, 3 pages. Retrieved on Oct. 3, 2021. Retrieved from the internet [URL: https://blockchainhealthcaretoday.com/index.php/journal/article/view/122/144 ].

Heath, SolarWinds hack was 'largest and most sophisticated attack' ever—Microsoft president, Financial Post, dated Feb. 14, 2021, 3 pages. Retrieved on Oct. 3, 2021. Retrieved from the internet [URL: https://financialpost.com/pmn/business-pmn/solarwinds-hack-was-largest-and-most-sophisticated-attack-ever-microsoft-president ].

COVID-19 Credentials Initiative, Hello World from the COVID-19 Credentials Initiative, dated Jun. 25, 2020, 3 pages. Retrieved on Oct. 3, 2021. Retrieved from the internet [URL: https://cci-2020.medium.com/hello-world-from-the-covid-19-credentials-initiative-6d45534c4b3a ].

Krebs, at Least 30,000 U.S. Organizations Newly Hacked Via Holes in Microsoft's Email, Krebson Security, dated Mar. 5, 2021, 6 pages. Retrieved on Oct. 3, 2021. Retrieved from the internet. [URL: https://krebsonsecurity.com/2021/03/at-least-30000-u-s-organizations-newly-hacked-via-holes-in-microsofts-email-software/ ].

* cited by examiner

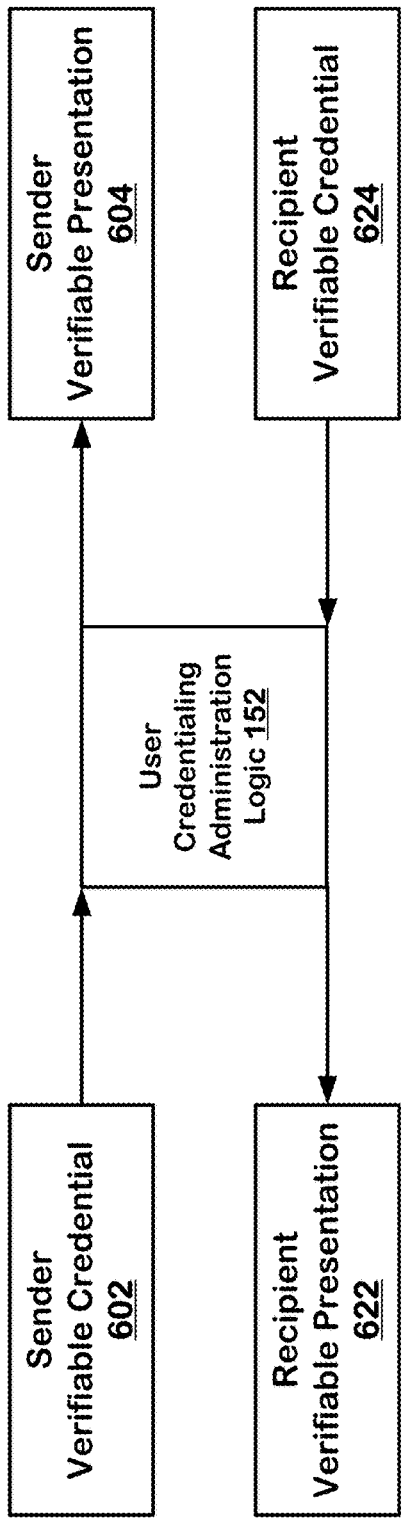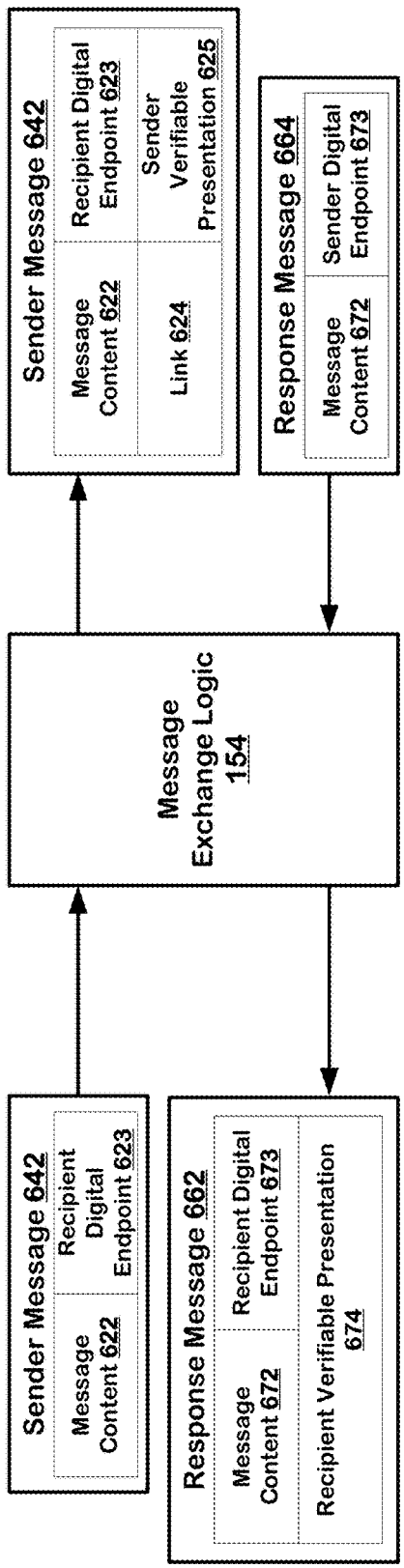

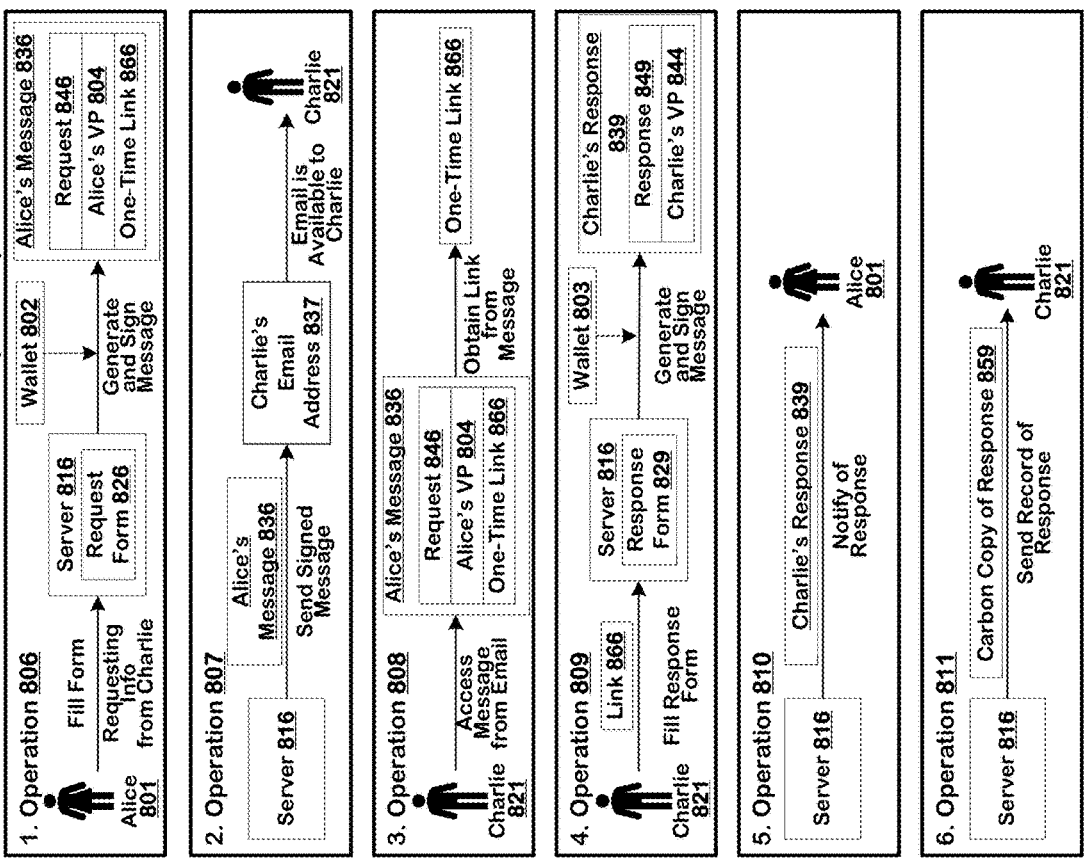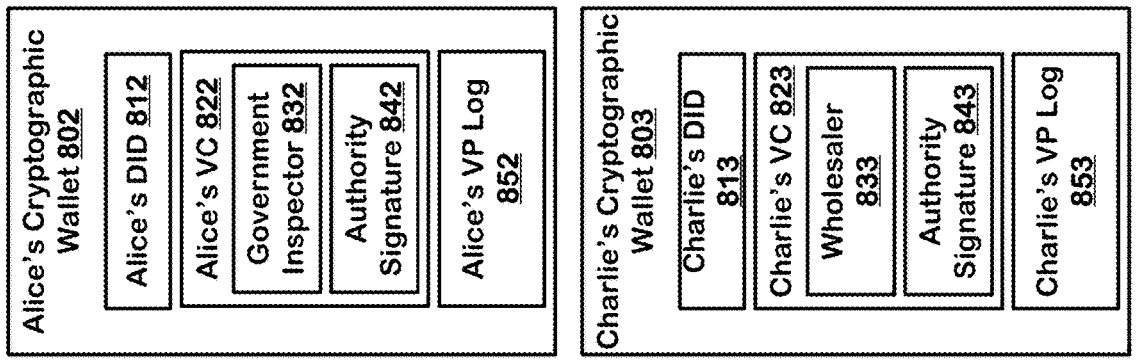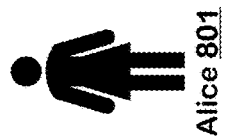
FIG. 8

FIG. 11

Example Response Message 1100

Webpage 1102

XATP

Tracing Request 1104

Drug Tracing Request from (CompanyName)

This is an official tracing request under the DSCSA from {RequesterName}, a {organizationType} located at {streetAddress}, {addressLocality}, {addressRegion}. Please respond within 24 hours using the buttons below. For more information about DSCSA tracing, please contact info@xatp.org or review the [link].

Tracing Request Summary

- Requester Name
- Requester Address
- Requester City
- Requester State
- Requester ATP Type
- Request ID
- Request Timestamp
- Reason for Request
- Suspect Description
- 3911 Incident Number
- Tracing Output Type
- GTIN
- Drug Name
- Lot Number
- Expiration Date
- Serial Number Tracing Request Content 1128

SUBMIT TRACING RESPONSE

Button Click Re-Direct to Submit a New Tracing Response 1144

Example Response Message Record 1200

Webpage 1202

For Your Records: Drug Tracing Response

The following is the response submitted to (legalName) regarding Tracing Request # (TracingRequestID). A brief summary is outlined below; the full tracing response can be found on your xATP portal or the attached file.

Tracing Response Summary

- Responder Name
- Responder Address
- Responder City
- Responder State
- Responder ATP Type
- Request ID
- Response Timestamp
- Ownership From GLN
- Ownership From Company Name
- Ownership From Company Address
- Ownership From Company Digital Contact Information
- Ownership To GLN
- Ownership To Company Name
- Ownership To Company Address
- Ownership To Company Digital Contact Information
- NDC
- GTIN
- Drug Name
- Lot Number
- Expiration Date
- Serial Number The full interoperable tracing response is attached to this email as a JSON file, and includes the full credentials of the responder. The tracing response is verifiable, presentable and part of an open standard deployed by the Partnership for DSCSA Governance and the Open Credentialing Initiative.

Tracing Response Content 1228

Tracing Response Carbon Copy 1204

FIG. 12

VERIFIABLE CREDENTIALLING AND MESSAGE CONTENT PROVENANCE AUTHENTICATION

CROSS-REFERENCE

This application claims the benefit of U.S. Provisional Patent Application No. 63/398,455, titled "Verifiable Credential-Enhanced Message and Magic Link Exchange", filed Aug. 16, 2022, which is hereby incorporated by reference for all purposes.

This application is a Continuation-In-Part of U.S. Non-Provisional patent application Ser. No. 17/492,488, titled "Decentralized Identity Authentication Framework for Distributed Data", filed Oct. 1, 2021, which claims the benefit of U.S. Provisional Patent Application No. 63/122,875, titled "Granting and Revoking Credentials in a Blockchain Network using Password Protected Truncated Data to Certify Paperwork and Trust Triplets Identity Authentication Framework", filed Dec. 8, 2020, and is also a continuation-in-part of U.S. Non-Provisional patent application Ser. No. 17/384,585, titled "Secure Messaging in a Machine Learning Blockchain Network", filed Jul. 23, 2021, which is a continuation of U.S. Non-Provisional patent application Ser. No. 17/063,605, titled "Secure Messaging in a Machine Learning Blockchain Network", filed Oct. 5 2020, now U.S. Pat. No. 11,081,219, issued Aug. 3, 2021, which claims the benefit of U.S. Provisional Patent Application No. 62/961,594, titled "Supply Chain Tracking and Management Using Blockchain Technology", filed Jan. 15, 2020, all of which applications are hereby incorporated by reference for all purposes.

INCORPORATIONS

The following materials are incorporated herein by reference in their entirety for all purposes:
  The Decentralized Identity Foundation, "KERI Made Easy", KERI Documentation, //identity.foundation/keri/docs/KERI-made-easy.html;
  GLEIF, "Introducing the verifiable LEI (vLEI)", //www.gleif.org/en/vlei/introducing-the-verifiable-lei-vlei; and
  Jespersen et al., "Traceability Vocabulary v0.1", World Wide Web Consortium, //w3c-ccg.github.io/traceability-vocab/ (Accessed Aug. 8, 2023).

FIELD OF THE TECHNOLOGY DISCLOSED

The technology disclosed generally relates to verifiable credentialing and message content provenance authentication, and more specifically to leveraging decentralized identity authentication of verifiable credentials to achieve bidirectional authentication between two actors and content provenance authentication leveraging a messaging platform, verifiable credentials, and secure web endpoints.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Stolen credentials are by far a top tactic for hackers, with approximately 80% of data breaches involving stolen or brute-forced credentials. Credential stuffing (i.e., the automated injection of stolen username and password pairs into website login forms) and phishing (i.e., impersonating legitimate websites in order to trick users into revealing personal information) are on the rise, both of which are typically dependent on the existence of passwords. Poor passwords are easy to guess or obtain, and users often undertake poor security behaviors, such as setting weak and/or recycled passwords across accounts.

A yet further challenge in today's information environment is the omnipresent threat of mis-information and dis-information. A malevolent actor, having gained access to a message or other information, may seek not only to profit from knowledge of the content therein, but to surreptitiously alter the contents, providing the recipients with some new form of the message not originally intended by the sender.

An opportunity arises for improving upon conventional methods of authentication. Yet further, new and novel aspects of sharing provenance among messaging (and other applications) participants can provide content provenance authentication.

BRIEF DESCRIPTION OF THE DRAWINGS

In the drawings, like reference characters generally refer to like parts throughout the different views. Also, the drawings ae not necessarily to scale, with an emphasis instead generally being placed upon illustrating the principles of the technology disclosed. In the following description, various implementations of the technology disclosed are described with reference to the following drawings.

FIG. 6A shows an architectural level schematic of a system component for a user credentialing administration logic, in accordance with one implementation of the technology disclosed.

FIG. 6B shows an architectural level schematic of a system component for a message exchange logic, in accordance with one implementation of the technology disclosed.

FIG. 8 shows a schematic illustrating an example implementation for the technology disclosed.

FIG. 11 is an example of a GUI for a secure web interface that allows for a recipient user to generate a response message to be transmitted back to a sender user.

FIG. 12 is an example of a GUI for a secure web interface displaying a carbon copy of a response message for the recipient user.

DETAILED DESCRIPTION

Figure 1:
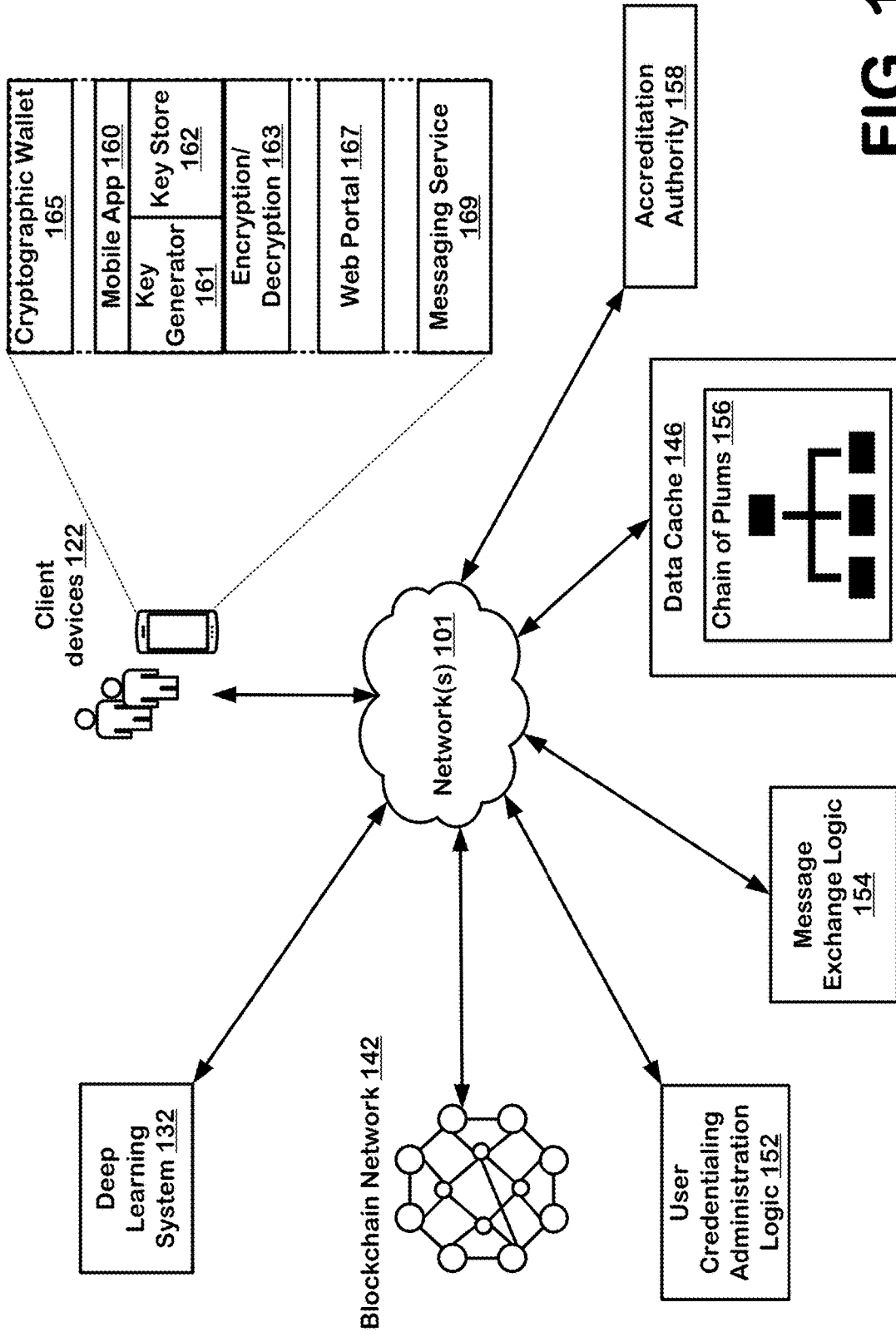
FIG. 1 shows an architectural level schematic of a system for verifiable credentialing and message content provenance authentication, in accordance with one implementation of the technology disclosed.

The following detailed description is made with reference to the figures. Sample implementations are described to illustrate the technology disclosed, not to limit its scope, which is defined by the claims. Those of ordinary skill in the art will recognize a variety of equivalent variations on the description that follows.

Data breaches involving stolen or brute-forced credentials are on the rise. In one example, credential stuffing tactics involving automated injection of stolen username and password pairs into website login forms are increasingly common. This may be, in part, due to bad actors utilizing novel technology (e.g., artificial intelligence) to improve the speed and stealth of brute-force methods. In addition, other tactics like phishing are also occurring more frequently. Phishing attacks involve fraudulently acquiring sensitive information from web users via impersonating legitimate websites and tricking the users into exposing sensitive information. Credential stuffing, phishing, and a large number of other cyberattacking strategies are typically dependent on the existence of passwords. Users often undertake poor security behaviors, such as setting weak and/or recycled passwords across multiple accounts. Poor passwords are easy to guess or obtain and requiring increasingly complicated passwords can make users more likely to recycle passwords.

As a result, there is a desire on the part of many organizations to move beyond passwords and other conventional approaches to authentication. Seeking instead to implement passwordless authentication, implementations can support removing the need for the user to enter any login credentials to sign in. Passwordless authentication methods may involve the use of biometric factors (e.g., FaceID), possession factors (e.g., a private key being held on a user's device), and "magic links". So-called magic links entail sending the user a URL directing to a one-time-use embedded toke via a messaging platform, such as email or text messaging. A magic link can be a method of passwordless authentication involving entering a user identifier (e.g., email address) at a sign-in screen on a web endpoint, receiving a message with a one-time pin (OTP) code, and using that OTP code to sign in.

Other forms of passwordless authentication that use OTP codes exist, as well as magic links that avoid the use of OTP codes such as XATP tracing. XATP tracing allows for the magic link to be accessed an indeterminate number of times, but only used for authentication once. Magic links have applications other than login and authentication; for example, giving the holder of a magic link the ability to enter data into an application without password-based authentication. At a high level, logging into a service using a magic link often takes the form of the following three steps: the user entering their email address at a sign-in screen on a web endpoint, the user receives an email with a magic link, and the user opens the email and clicks the magic link to complete the sign-in process.

While magic links may offer stronger protection than passwords, they introduce several security issues as well. Security is tied to the user's messaging account, such as an email address. Mail servers are themselves frequently insecure, and the emails might be visible to employees at the user's email provider. The email account itself may be compromised via a number of routes, such as a bad actor accessing the user's inbox on an unattended or stolen device. Users are able to share links and there is nothing stopping a magic link email recipient from forwarding the email, sending the link, or sharing the OTP code with a bad actor. Phishing attacks have evolved to incorporate deceiving users into providing this information in order to fraudulently obtain the user's personal information. Magic links are also vulnerable to man-in-the-middle attacks. For instance, unless users access their email through encrypted networks, hackers can intercept less secure connections and steal the session token from a magic link.

Moreover, magic links specifically (and passwordless authentication generally) tend to enable authentication for registered users on a given system; recipients who are not registered as part of the system are unable to participate. As a result, participants from disparate systems are unable to mutually authenticate each other without needing to register on one system or another (which may not be feasible), and thus fall back on insecure and unreliable methods of information exchange. New solutions are needed to address the security and feasibility problems associated with magic links.

The technology disclosed addresses these problems by extending and enhancing magic links with tooling such as Verifiable Credentials (VC)—anchoring passwordless authentication over legacy channels with decentralized (e.g., self-sovereign) cryptographic materials, capable of being supported by a decentralized data store. A VC is a proof of what you are (e.g., a pharmacist or an attorney), as determined by a trusted identity authenticator. For instance, even if a bad actor obtains access to an attorney's email account, they still have no VC demonstrating a license to practice law. The technology disclosed, as a result, makes magic link systems the backbone of interoperable, authenticated, and identity linked-information exchange.

The disclosed system and methods address several fundamental flaws with messaging systems, such as email, SMS, and other legacy channels where spoofing and phishing are common. By anchoring authentication in VCs, this approach effectively represents a second authentication factor in addition to whatever trust participants might place in sending to (or receiving from) a given messaging system (e.g., email) address. This is a superior means of two factor authentication than other channels such as SMS, as it can be entirely decentralized and is less vulnerable to network attacks.

In using the technology disclosed, the authentication process remains secure even if the messaging system account is compromised, because the bad actor still requires access to a relevant VC. Moreover, the technology disclosed allows for authentication leveraging VCs on an open schema, therefore enabling interoperability between participants from disparate systems without demanding registration on centralized services or falling back on insecure and/or unreliable methods of information exchange.

Many implementations of the technology disclosed rely on a decentralized identity schema under which a decentralized identifier (DID) and its associated DID document provides user identifiers and/or public keys used in an identity proof and a CV is a proof of credentials, as determined by a trusted identity authenticator. In some implementations, the technology disclosed relies on DIDcomm (a protocol for creating secure communication channels between software controlled by DID-controlling entities from diverse DID-based systems, which can be people, organizations, or things) as a direct method for communication between holders of VCs. While DIDcomm is a mature protocol, adoption and integration into production systems remains in an early stage. To take advantage of VCs today, one realistically must fall on more ad hoc approaches until adoption has hit a point where DIDcomm is possible at scale, and address drawbacks accordingly. Other implementations of the technology disclosed provides a solution to this problem via a method to combine VCs with legacy channels to support.

The technology disclosed can further be implemented by sharing a Verifiable Presentation for purposes of authentication, changing the method of integrating the Verifiable Presentation with the message and/or using a standard that is similar to a VC, but not exactly the same; e.g., a more general or different cryptographic proof of identity.

The technology disclosed can implement verifiable credentials (VC) of various VC types, such as a self-sovereign or an entity-sovereign, a World Wide Web Consortium (w3c) adherent, a Zero-Knowledge Proof (ZKP), a Key Event Receipt Infrastructure (KERI) microledger based, a partially obscured or a fractional VC and a Legal Entity Identifier (LEI) or a Global Legal Entity Identifier (GLEIF) adherent.

A system and methods for the technology disclosed are described below. First, certain terminology and concepts will be introduced to complement later-described aspects of the technology disclosed. Next, a system for the technology disclosed is described, in accordance with one implementation of the technology disclosed. The description continues to expand upon this system with variations to the system and selected example implementations of the technology disclosed.

Terminology

The technology disclosed provides systems and methods for leveraging decentralized credentials to achieve bidirectional authentication between two actors leveraging a messaging platform/system, such as email or another text-based system, Verifiable Credentials (VCs), and secure web endpoints. The technology disclosed empowers one party (referred to herein as the "Sender") to send a message enclosed with a Verifiable Presentation which allows another party (referred to herein as the "Recipient") to authenticate the message's provenance and the identity of the sender. Moreover, the message contains a link to a secure web endpoint, where the recipient can submit a response signed by their own Verifiable Presentation, allowing the Sender to authenticate the identity of the Recipient. In this way, both participants are able to authenticate each other's identities with an additional factor of authentication such that neither participant is required to register with a particular service.

Decentralized identifiers (DIDs) are a type of globally unique identifier that enables an entity to be identified in a manner that is verifiable, persistent (as long as the DID controller desires), and does not require the use of a centralized registry. (See e.g., //www.w3.org/TR/did-core/incorporated herein by reference for all purposes), DIDs enable a new model of decentralized digital identity that is often referred to as self-sovereign identity or decentralized identity. (See e.g., //ec.europa.eu/futurium/en/system/files/ged/eidas_supported_ssi_may_2019_0.pdf incorporated herein by reference for all purposes), They are an important component of decentralized web applications.

The technology disclosed includes various approaches to decentralized identity authentication and management used for accessing, creating, and maintaining private, shared, and sensitive documents. Decentralized identifiers (DIDs) can be assigned to authenticated users, each contributing their associated public keys to form a public key registry. In some implementations, the public key registry establishes a registry node; registry nodes may be replicated and/or stored in a blockchain or other distributed ledger. Alternatively, the registry nodes can be implemented with databases, relational or object-oriented, other data structures, or combinations thereof. In some implementations, registry nodes can interact with other registry nodes subject to the governance of an agreed trust framework (i.e., enabling interoperability between participants from disparate systems without demanding registration on centralized services).

Furthermore, the disclosed implementations herein can, but are not limited to, include decentralized systems and methods that implement the DIDs and associated VCs that may be stored, evaluated, updated, and authenticated, such as distributed/decentralized ledgers like blockchain. Typically, these ledgers are implemented as blockchains that record a DID document corresponding to a DID. The DID document generally lists public keys for the DID. Documents can be stored, for example, using a data structure comprised of a network of nodes, such as a permissioned blockchain, and in certain implementations, permissioned blockchain storing data accessible to authenticating actors, shared among enterprises, to validate identities and/or credentials in high security and/or high data integrity applications.

VCs can be gathered from the requestors themselves, or more commonly, licensing bodies, professional certification bodies, regulatory agencies, and the like. VCs can be implemented using DIDs, e.g., a DID is implemented in embodiments using a uniform resource identifier (URI) having the form "did:<did-method-name>:<content>", which identifies a particular entity (e.g., a human, a server, a logical object, a physical object). Associated with a DID is a DID document listing associated public keys. The DID document corresponding to a DID is obtained through a process called "DID resolution", which is specific to the DID method. The DID document could be derived from the DID itself (as in did:key) or downloaded from a web server (as in did:web) or retrieved from a public blockchain (as in did:ethr). DID resolution involves producing a canonical DID document from the public key itself, with no need to query a server. For example, a DID defined by—did:web:w3c.xyz might translate into a URL //w3c.xyz/.well-known/did.json, in which case DID resolution involves a HTTP GET of that URL. When the user seeks to access data in the permissioned private data structure on behalf of her enterprise, she attaches the VC. The recipient server upon receiving the request to access data by the requestor can initiate a transaction with the registry to verify the VC. Some applications relate to pharmaceuticals, artificial heart valves and other compositions, systems and apparatus for medical uses and other high security, high data integrity applications.

The technology disclosed can employ decentralized identity authentication (i.e., leveraging self-sovereign credentials to achieve bidirectional authentication between two actors using a messaging platform, VCs, and secure web endpoints) to enable a Sender and a Recipient to authenticate each other's identity with an additional factor of authentication. Within authentication systems, users are able to authenticate themselves to verify their identity in order to access a service or resource. Once registered within a service (i.e., granted a token and credentials, often including certain access credentials authorizing the user to access specific data or functions), a user may authenticate themselves to access the service by providing one or more previously enrolled authentication factors to an authentication server. At the simplest level, authentication may involve a single factor; i.e., only requiring one authentication factor in order to authenticate a user such as a knowledge factor (e.g., password, passphrase, personal identification number (PIN), security questions, etc.), a possession factor (e.g., ID card, physical keystore, user device provisioned with a built-in hardware token or a software token, etc.), or an inherence factor (e.g., a biometric input like FaceID or a fingerprint scan).

In its infancy, single-factor authentication was frequently implemented in the form of a username and password. However, this system was quickly and easily infiltrated by bad actors via obtaining user passwords. Over time, authentication systems have evolved to request multiple authentication factors (i.e., multi-factor authentication; MFA) and/or implement more rigorous requirements for the format of an authentication factor. More stringent authentication requirements and MFA systems have increased digital security for registered users of a system but are not without weaknesses and still do not prevent breaches of user credentials.

In particular, attempts to improve the conventional password have proven complicated. Password requirements such as frequent expiration of passwords, rejecting recycled passwords or easily guessed words/phrases, and specific constraints on password content (e.g., minimum character length or inclusion of a capital letter, number, special character, etc.) often result in users failing to remember passwords, preventing their utility. Moreover, users may try to remediate this issue by recording passwords in a vulnerable location, such as a handwritten note or a text file on their personal device, where they are easily accessible to bad actors. When users are asked to remember a large volume of passwords for various services, they are more likely to select passwords that are as simple as allowed by the given constraints; hence, these passwords are easy to obtain by others. These issues, amongst others, have not been sufficiently addressed over time, and cyberattacks targeted at obtaining user passwords have steadily increased over time. Thus, a more attainable goal is a secure form of passwordless authentication.

Passwordless authentication methods frequently rely on strong authentication factors, comparatively speaking. In one example, users may bypass the need for a password to authenticate themselves by enrolling a biometric factor. Despite promise, biometric factors are not always as secure as expected when introduced. Advancements in technology have enabled bad actors to closely replicate biometric factors like voice recognition and facial scans (so-called "deepfakes") and higher-security biometric factors like retinal scans, gait, or genetic data are characterized by substantial monetary cost and resource demand. In another example, users are provided with a magic link (sent via email, SMS, and so on) that enable the user to authenticate themselves via the use of OTP codes or XATP tracing.

Magic link systems are advantageous in passwordless authentication in that they are relatively straightforward and accessible to implement in most scenarios (comparatively speaking to many other forms of passwordless authentication). The disadvantages of magic link systems, as described above, include security risks such as reliance on messaging system security and vulnerability to man-in-the-middle attacks. Moreover, magic links specifically (and passwordless authentication generally) tend to enable authentication for registered users on a given system; recipients who are not registered as part of the system are unable to participate. As a result, participants from disparate systems are unable to mutually authenticate each other without needing to register on one system or another (which may not be feasible), and thus fall back on insecure and unreliable methods of information exchange. New solutions are needed to address the security and feasibility problems associated with magic links.

The technology disclosed addresses these problems by extending and enhancing magic links with tooling such as Verifiable Credentials (VC)—anchoring passwordless authentication over legacy channels with decentralized (e.g., self-sovereign) cryptographic materials, capable of being supported by a decentralized data store. In many implementations, widely implemented standards for VCs such as W3C are applicable. VCs are an open standard for digital credentials that can represent both tangible (e.g., a passport) and intangible (e.g., a license to practice) credentials. VCs are verified by trusted identity authenticators (for instance, in the form of a digital signature) and implementable within decentralized systems. VCs can be represented within a "triangle of trust" model consisting of an "Issuer" (i.e., the entity that generates the credential), a "Holder" (i.e., the entity that uses the credential to create a presentation of proof for the credential), and a "Verifier" (i.e., the entity that requests proof of credentials from the Holder). Any role in the triangle can be filled by a person, an individual, a device, and so on. The triangle of trust model is built upon the principle that the Issuer trusts the Holder (i.e., provides and "vouches" for the credential), the Holder trusts the Verifier (i.e., presents their credentials), and the Verifier trusts the Issuer (i.e., views the credential as reputable).

In other implementations, the VCs associated with the disclosed systems and methods do not align with the most common definitions of a VC per say but are rather a comparable alternative to VCs in situations wherein the implementation of a VC is not technically feasible. For example, the VP may be associated with a Sender message in a manner other than via a verified cryptographic signature that depends on a DID. Alternatively, a broader or alternate cryptographic proof of identity may be used in place of a W3C adherent VC and/or VP.

Under a modern decentralized identity schema, a DID and its associated DID document provide the identifiers and public keys used in an identity proof. A VC is a proof of "what" someone is (e.g., a licensed clinician or a practicing attorney) that can be associated with a user's DID and may contain, for example, credential metadata (e.g., the DID of the Issuer, the type of credential, the issuance date, and so on), claims (e.g., information specific to the credentials addressed to the user's DID), and proofs (e.g., cryptographic signatures from the issuing authority that enable verification of the authentication and ownership of the credential).

VCs are cryptographically signed by trusted authorities; thus, they are effectively tamper-proof. When validating a VC, both the Holder and the Verifier are self-sovereign because the interaction does not require contacting the Issuer. Additionally, the VC is portable and not limited to one registration service, enabling users in disparate enterprises to use a VC with others outside of their organization. Moreover, VCs can be standardized (i.e., the W3C Verifiable Credentials standard) which further enables their portability. However, the technology disclosed does not rely on standardization of VCs as a limitation of the VC interoperability. There are numerous routes by which a user is able to present their credentials, including privacy-preserving routes that enable minimum disclosure via only sharing a portion of the user's VC. In this scenario, a user may send a Verifiable Presentation of a particular credential rather than the entirety of their VC.

Generally speaking, a Verifiable Presentation (VP) often includes claims (or a single claim) extracted from a VC. The VP may include claims extracted from more than one VC, and the claims may be from the same or different issuers. If a VC is presented directly from a Holder to a Verifier, the VC becomes a VP. Hence, the Holder of the VC has control over the extent of data that is presented in the VP (e.g., one particular claim, multiple particular claims, or all claims within the VC) and shared with the Verifier. Herein, the term Sender (alternatively, "sender user)") is used synonymously with Holder, and Recipient (alternatively, "recipient user") is used synonymously with Verifier.

Many implementations of the technology disclosed involve a Recipient receiving a message that contains the Sender's VP from the Sender via a messaging system. A user skilled in the art will recognize that a range of messaging systems exist that may be used to implement the technology disclosed, such as email, SMS (also referred to herein as "text messaging"), instant messaging platforms, secure messaging servers and other routes of private direct messaging, peer-to-peer or client-server architectures, encrypted or non-encrypted protocols, and so on. Though not limiting, the examples described herein will refer primarily to email, and occasionally SMS, as the messaging system, for simplicity.

In certain implementations, the message sent from the Sender to the Recipient may contain, in addition to data relating to the Sender's DID and VP, authentication information comprising a reference to a plum resident in a data cache. Herein, the term "plum" refers to a hash-addressable, hash-verifiable chained data structure resident in a data cache that stores content provenance for the message. The plum contains a head and a head seal comprising a hash value of the head, metadata and a metadata seal comprising a hash value of the metadata, one or more relations and a relations seal comprising a hash value of the relations, and a body and a body seal comprising a hash value of the body. For each message version created and signed using a verified signature of a sender user, a new plum is added to the data cache and chained to an ancestor of a prior message version, thereby forming a chain of plums.

A message exchange logic configured to mediate transmission of the message from the sender user to the recipient user (expanded upon further in the description below) can be further configured in some implementations to iterate through a chain of plums until a plum corresponding to a message version whose content provenance is to be authenticated is reached. In one implementation, the message exchange logic is further configured to iterate through a chain of plums until multiple plums corresponding to message versions whose content provenance is to be authenticated are reached. Accordingly, for sending a message on behalf of a sender user seeking to send a message, the message exchange logic can be further configured to prompt the Sender for their verified signature and message content, instantiate a plum, incorporate the message content and the digital identifier of the Sender into the body, compute a body seal hash of the body, compute a head seal hash value for the plum, and add the plum to the data cache. To add a new version of the message, the message exchange logic can be further configured to instantiate a child plum, populate the body with new version message content and the verified signature of the Sender, incorporate relation information of the prior version message as a parent plum, compute a body hash seal of the body for the child plum, a relations seal hash value of the relations information for the child plum, and a head seal hash value for the child plum and add the child plum to the data cache. Within a chain of related plums, a difference can be tracked by each corresponding plum between metadata and content of a version and the metadata and content of a previous version.

The message exchange logic may authenticate content provenance of a message, on behalf of a recipient user, by iterating through the chain of plums (beginning with an ancestral plum) until a plum, or many plums, corresponding to the message version(s) whose content provenance is to be authenticated is/are reached. For each plum in the chain of plums, the message exchange logic may verify matching corresponding data entries for at least one of a nonce, a subject, an ancestral relationship, and a verified signature. Concordance with other plums in the chain of plums of owned data for the plum may be verified, including the DID, previously owned data, and/or additional metadata. The verified signature of a user can include a VP and a DID of the user. Each time the verified signature is validated, the plum can maintain a time stamp. This message exchange does not require either the Sender or the Recipient to establish an account (i.e., register or enroll) on the server, nor do the Sender and Recipient need to have prior knowledge of one another.

The message exchange logic, in certain implementations, may maintain at least one of the following: a whitelist for users, a blacklist for users, a whitelist of credential types, and/or a blacklist of credential types.

Many of the implementations of the technology disclosed described herein with reference to the figures rely on a traditional representation of verifiable credentials, i.e., VCs linked to DIDs that leverage self-sovereign identities and may rely on protocols and systems that are recognizable to a user skilled in the art, including (but not limited to) DIDComm (a communication protocol for creating secure communication channels between software controlled by DID-controlling entities from diverse DID-based systems), the self-sovereign identity model (expanded upon with reference to FIG. 5), the W3C VC model (a widely-used recommendation for VC data models), zero-knowledge proof protocol (credential proofs that prove veracity of a claim without revealing the content of the claim itself), partially obscured or fractional VCs, microcredentials, KERI microledgers (Key Event Receipt Infrastructure), verifiable Legal Entity Identifiers and/or standards and recommendations from the Global Legal Entity Identifier Foundation, and so on.

It is readily apparent that a large variety of models and protocols exist for the implementation of VCs. Some are mature while others are newly established, but very few are adopted to the extent that it is feasible to implement at scale. The technology disclosed solves this problem by introducing an approach that is highly interoperable; that is, the disclosed systems and methods do not rely on any one particular digital identity system. Furthermore, the technology disclosed is configured such that it may be implemented within existing legacy channels and is not dependent on the relevant production system(s) and/or enterprises having adopted or integrated any particular digital identity protocol.

As stated above, the disclosed approach is primarily described with reference to the figures in the context of various widely-implemented identity models, such as self-sovereign identity and DID-based systems. It is to be understood that this is purely for the convenience of the reader and providing an illustrative description of the features disclosed herein. In contrast to highly-individualized situations unique to a particular organization's identity management structure, the descriptions of which may be highly abstract, difficult to conceptualize, or infeasibly varied in number, the descriptions herein primarily refer to implementations comprising mature identity models and protocols for simplicity and clarity of description. However, it will be readily apparent to a user skilled in the art that the technology disclosed is by no means limited to these protocols and designed such that the approach may be compatible with existing identity systems that are not dependent on substantial changes in identity management architecture within an enterprise. Accordingly, the reader will intermittently be directed towards aspects and features of the technology disclosed with alternative implementations to those used as educational examples herein.

A user skilled in the art will recognize that many variations of the above-described technology exist, and the disclosed implementations herein may comprise a range of architectural and ensemble structures without deviating from the scope or spirit of the technology. The mention of certain terminology or implementations of said terminology alone should not be understood to imply universal or limiting aspects of the technology disclosed; rather, merely as introductory concepts to build upon later in the description.

Now, the discussion turns to a description of the disclosed system and methods in further detail.

System Overview

FIG. 1 shows an architectural level schematic of a system 100 for verifiable credentialing and message content provenance authentication, in accordance with one implementation of the technology disclosed.

Because FIG. 1 is an architectural diagram, certain details are intentionally omitted to improve the clarity of the description. The discussion of FIG. 1 is organized as follows. First, the elements of the figure are described, followed by their interconnections. Then, the use of elements in the system is described in greater detail.

System 100 includes one or more client devices 122, deep learning system 132, blockchain network 142, user credentialing administration logic 152, and message exchange logic 154. System 100 also includes a data cache 146 storing a chain of plums 156 and an accreditation authority 158. Client device(s) 122 can be used to access at least one of a user's cryptographic wallet 165, a mobile app 160 (comprising key generator 161, key store 162, encryption/decryption 163), a web portal 167, and/or a messaging service 169. Various implementations of the technology disclosed include the use of differing combinations of services and applications via the client device(s) 122 and none of the listed services and applications 165, 160, 167, or 169 are required components of the technology disclosed.

System 100 also has network 101 which can be a public network or a private network, in different implementations. System 100 can include multiple applications and multiple networks.

In the interconnection of the elements of system 101, network 112 couples client device(s) 122 (e.g., a computer, tablet, cell phone, or smartwatch) with the disclosed technology components 132, 142, 152, 154, 146, and 158. The communication path can be point-to-point over public and/or private networks. Communication can occur over a variety of networks, e.g., private networks, VPN, MPLS circuit, or Internet, and can use appropriate application program interfaces (APIs) and data interchange formats, e.g., REST, JSON, XML, SOAP. The communications can be encrypted. This communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX.

Further continuing with the description of the system 100, components of FIG. 1 are implemented by software running on varying types of computing devices. Example devices are a workstation, a server, a computing cluster, a blade server, and a server farm, or any other data processing system or computing device. The engine can be communicably coupled to the databases via a different network connection.

While system 100 is described with reference to particular blocks, it is to be understood that the blocks are defined for convenience of description and are not intended to require a particular physical arrangement of component parts. Further, the blocks need not correspond to physically distinct components. To the extent that physically distinct components are used, connections between components can be wired and/or wireless as desired. The different elements or components can be combined into single software modules and multiple software modules can run on the same hardware.

Next, the function of the components of FIG. 1 are introduced. The functionality will be described within the context of two example users, a sender user ("Sender") and a recipient user ("Recipient"). System 100 can be leveraged to achieve bidirectional authentication between the Sender and the Recipient, each possessing their own respective decentralized credentials, via the use of a messaging service 169 (e.g., email). The respective VCs of the Sender and Recipient are signed by accreditation authority 158. One accreditation authority 158 is shown in FIG. 1 for simplicity; however, each respective user may possess any number of VCs that are each respectively issued by an accreditation authority 158 and different VCs may be issued by the same, or different, accreditation authority/authorities 158. The decentralized identity and credentials of the various users stored in respective cryptographic wallets 165 can be verified using public key cryptography anchored on a distributed ledger such as blockchain 142. Decentralized identifiers and credentials are described in more detail with reference to FIGS. 2-5.

Sender can access web portal 167 via a client device 122 and log into a secure website that allows Sender to generate a message for the Recipient. Web portal 167 is able to access Sender's cryptographic wallet 165, which stores a DID and a VC for the Sender. User credentialing administration logic 152 can generate, after obtaining the VC from the Sender's cryptographic wallet 165, a VP of the Sender's credential. The VP is sent to the message exchange logic 154, and the message exchange logic 154 generates a one-time-use link containing query parameters that uniquely identify the parameters of the Sender's message (i.e., the DID of the Sender, the Universal Unique Identifier (UUID) of the Sender message, a one-time authentication token, and additional authentication information).

The message exchange logic 154 combines the Sender message, the VP, and the link with query parameters and sends the message to Recipient (e.g., using the Recipient's email address). The Recipient is able to access the Sender message using a web portal 167 on a client device 122. The provenance and authenticity of the Sender message can be independently checked by verifying the VP, which is described in further detail below. Recipient clicks on the one-time-link contained within the Sender message, directing them to a secure web endpoint with a form accessed via web portal 167. Recipient is able to fill out a response on the form. Web portal 167 is able to access Recipient's cryptographic wallet 165, which stores a DID and a VC for the Recipient.

User credentialing administration logic 152 can generate, after obtaining the VC from the Recipient's cryptographic wallet 165, a VP of the Recipient's credential. The Recipient can then sign the Response Message (i.e., the filled-out form) using their VP. In one implementation, Recipient opts to allow the web portal 167 to access their cryptographic wallet 165 to obtain the Recipient VC. In another implementation, Recipient does not allow access to their cryptographic wallet 165 and chooses to generate the VP separately then copy and paste the VP to sign the response. After accepting and validating the Recipient VP as authentic, message exchange logic 154 notifies Sender with the response, providing interoperable and bidirectional authentication of the recipient's identity, without the need for them to create an account on the server for web portal 167. In one implementation, the technology disclosed can implement a credential that includes a claim that the digital endpoint is associated with the individual (e.g., a credential stating that Recipient is who they say they are, and their email address is correct). After being notified, Sender can view the response along with the VP. In some implementations, Recipient is also sent a "carbon copy" as a record of their response.

As messages are generated and transmitted between Sender and Recipient, message exchange logic 154 can instantiate a plum associated with a message that will be stored in a chain of plums 156 in a data cache 146. Data plumbing using the chain of plums 156 is further described with reference to FIGS. 13-19.

In some implementations, Sender and/or Recipient are asked to provide additional authentication factor(s) using Mobile App 160. Certain implementations of the technology disclosed may leverage deep learning system 132 to securely detect fraudulent use of VCs by observing patterns in the messages signed by them. These predictions may take the form of risk scores, which may be visible to the message Sender or Recipient, and may also factor in the time difference between when a VC and/or VP is/are issued, and the time that the link was opened. The use of artificial intelligence and deep learning to detect fraudulent use of self-sovereign identities is described further in U.S. Non-Provisional patent application Ser. No. 17/492,488, titled "Decentralized Identity Authentication Framework for Distributed Data", filed Oct. 1, 2021, the entirety of which is incorporated by reference.

The decentralized identity and verifiable credentialing schema utilized within many implementations of the technology disclosed will now be expanded upon. In other implementations, a variation of the decentralized identity and verifiable credentialing schema described below may be used. Various modifications to the disclosed implementations will be apparent, and the general principles defined herein may be applied to other implementations and applications without departing from the spirit and scope of the technology disclosed.

Verifiable Credentialing

The descriptions below with reference to FIGS. 2-5, as previously indicated, establish a foundation for certain implementations of the technology disclosed that leverage decentralized identity models such as self-sovereign identity. These models and conceptual foundations were selected as example implementations due to the accessibility of understanding said example implementations, not as limitations of the technology disclosed. In addition to the below-described models, the technology disclosed may be applied with or without DIDComm, with or without W3C, with or without LEI, with or without KERI microledgers, with or without ZKP, with alternative representations of a VC such as a "verifiable business card", and so on. See, for example, the documentation materials for KERI, LEI, and W3C, of which are incorporated herein in their entirety by reference for all purposes.

Figure 2:
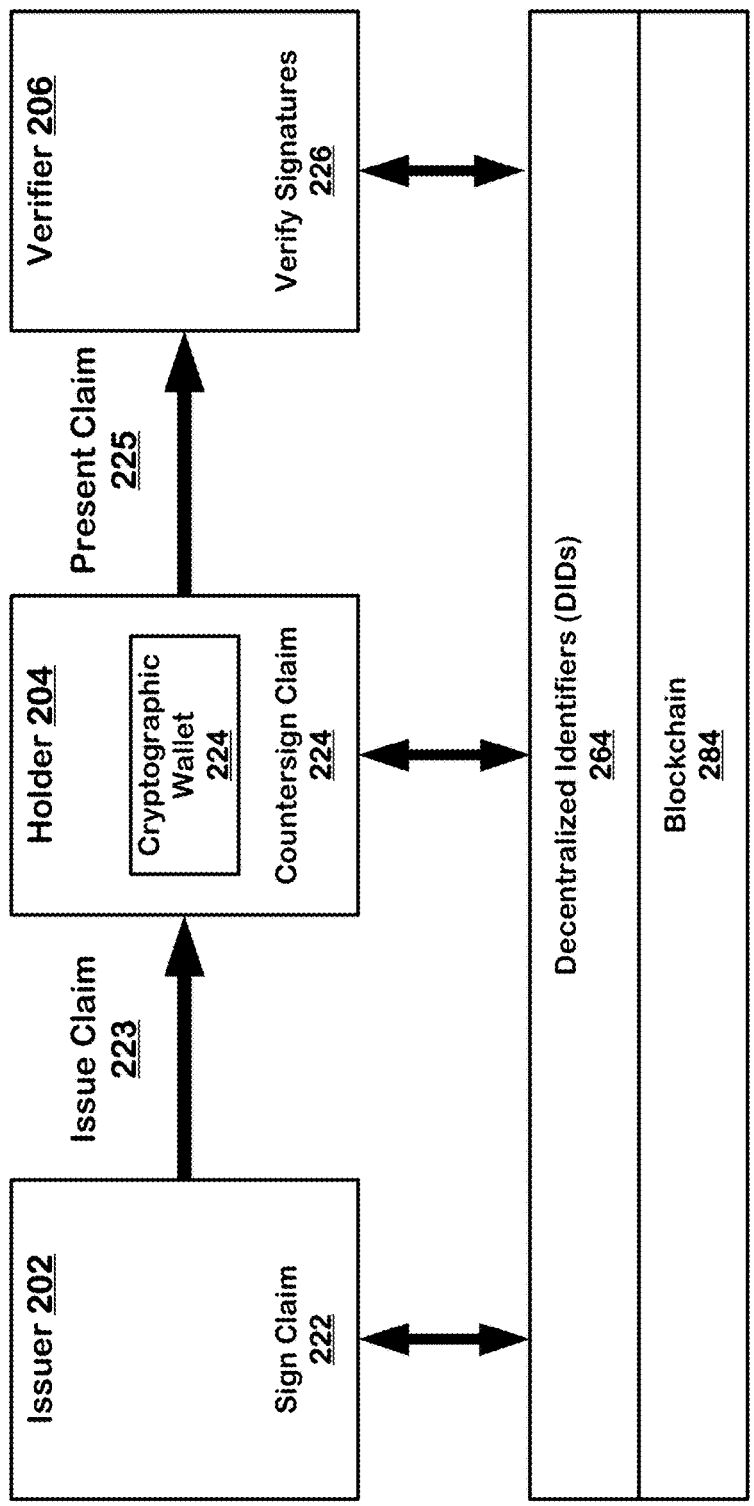
FIG. 2 shows a schematic illustrating a decentralized identity model, in accordance with one implementation of the technology disclosed.

FIG. 2 shows a schematic illustrating a decentralized identity model 200, in accordance with one implementation of the technology disclosed. Users within a decentralized identity model 200, e.g., Holder 204, can have respective decentralized identifiers (DIDs) 264 stored in a cryptographic wallet 224. The decentralized identity and credentials of the various users stored in respective cryptographic wallets 224 can be verified using public key cryptography anchored on a distributed ledger such as blockchain 284. An Issuer 202 (e.g., accreditation authority 158) may issue a VC 223 to Holder 204 and send the VC directly to be stored in Holder's cryptographic wallet 224. The VC is cryptographically signed 222 by the Issuer 202 to prove authenticity and ownership. Holder 204 chooses to present a VP 225 with Verifier 206, wherein the VP contains one or more claims extracted from the VC. Holder 204 cryptographically signs the VP. Verifier 206 can verify the signatures 226 of both Holder 204 and Issuer 202 through blockchain 284. The credibility of model 200 is based on trust—more specifically, Issuer 202 trusts and will vouch for Holder 204, Holder 204 trusts and will share a claim with Verifier 206, and Verifier 206 trusts the authority of Issuer 202 to verify the claim. This concept is illustrated within FIG. 3 containing a schematic of the so-called "triangle of trust" concept for VCs.

Figure 3:
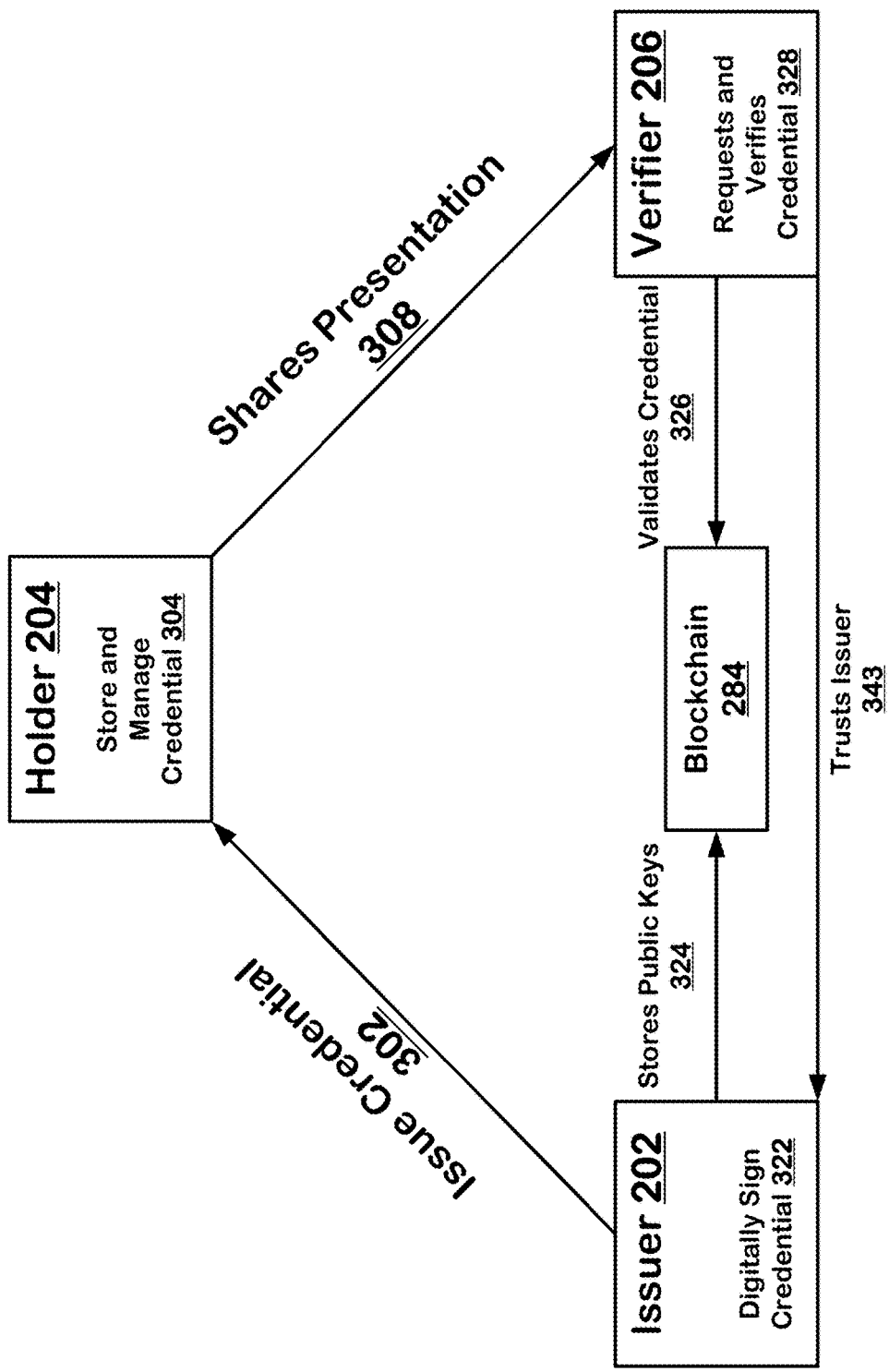
FIG. 3 shows a schematic illustrating a Verifiable Credential triangle of trust model, in accordance with one implementation of the technology disclosed.

FIG. 3 shows a schematic illustrating a Verifiable Credential triangle of trust model 300, in accordance with one implementation of the technology disclosed. Model 300 can be thought of as synonymous with model 200; however, they differ in that model 300 demonstrates the system of trust that enables the schema to function securely. Again, model 300 demonstrates that an Issuer 202 digitally signs a credential in operation 322 and issues said credential to the Holder 204 in operation 302. Issuer 202 stores public keys 324 within blockchain 284, enabling verification. Holder 204 stores and manages the credential in operation 304 (i.e., Holder's identity is self-sovereign). Holder 204 can share a presentation of their credential in operation 308 to Verifier 206 in response to Verifier 206 requesting the credential (and subsequently, verifying said credential) in operation 328. Verifier validates the credential via blockchain 284 in operation 326. Operations 324 and 326 effectively represent a trust relationship such that Verifier 206 is able to verify the credential because Verifier trusts the credibility of Issuer 202.

Figure 4:
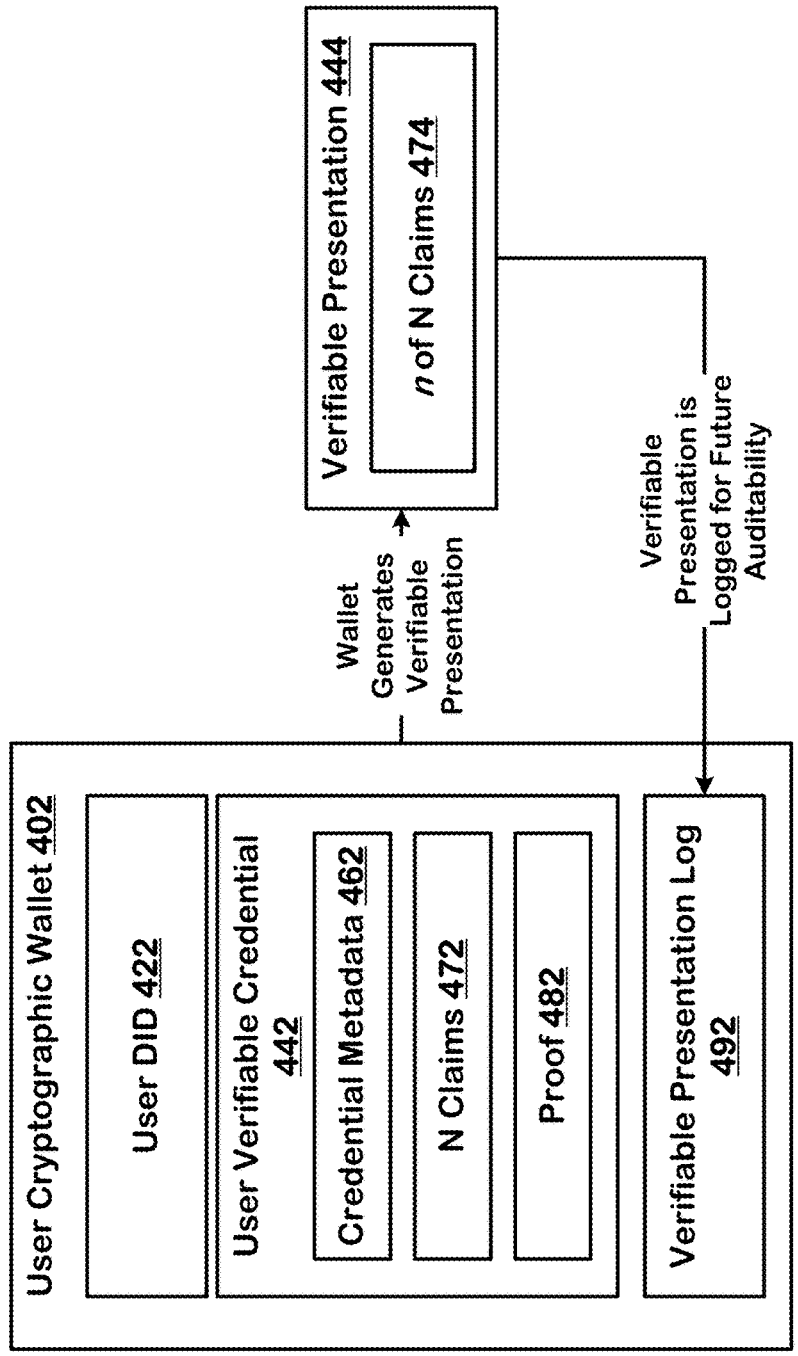
FIG. 4 is a simplified block diagram of a user's cryptographic wallet containing a Verifiable Credential, in accordance with one implementation of the technology disclosed.

In one example, Issuer 202 is a University from which Holder 204 has received a degree. Issuer 202 may issue a credential 302 to Holder 204, the credential containing a claim of the Holder's degree, and the credential 302 is signed by the Issuer 202 in operation 322 to legitimize the digital credential. If Holder 204 is applying for a job with Verifier 206 and Verifier 206 requests proof of a degree (i.e., operation 328), Holder 204 can share a VP of their degree (i.e., operation 308) with Verifier 206. Verifier 206 validates the credential (i.e., operation 326) by verifying both the Holder's signature and the Issuer's signature. Because Verifier 206 trusts the legitimacy of the University, the trust is accordingly extended to Holder 204 for their shared VP. FIG. 4 provides additional detail on the content of a Verifiable Credential.

FIG. 4 is a simplified block diagram 400 of a user's cryptographic wallet 402 containing a Verifiable Credential 442, in accordance with one implementation of the technology disclosed. User cryptographic wallet 402 can store at least one digital identifier for the user, i.e., user DID 422, one or more VCs 442 for the user, and a log 492 for each generation of a VP 444. The user DID (decentralized identifier) 422 is a type of identifier that enables an entity, such as a user or an enterprise, to be identified in a manner that is verifiable, standardized, and robust against tampering. User DID 422 is implementable independent of registration with any particular registry, identity provider, or certificate authority. DID 422 points to a DID Document (not shown) containing data; typically, the DID, a cryptographic public key, a verification/proof of identity, additional cryptographic/authentication information, and/or metadata. If the user wants to authenticate themselves using User DID 422, the public key associated with DID 422 can be used to verify the user's identity using public/private key pair cryptography leveraging a blockchain.

The user's DID 422 is associated with at least one VC 442 (Verifiable Credential) to identify that the user is the holder of the VC 442. The VC 442 is a standardized format of digitally represented credentials that are secured by cryptography, self-sovereign, and verifiable. VC 442 comprises three primary components: credential metadata 462, a number of claims 472, and proof(s) 482. Credential metadata 462 may contain, for example, information about the credential type, expiration date, and issuer (e.g., the issuer's DID). Claims 472 about the VC each represent information about the user and/or the credential, such as an identifier of the user or an attribute of the user's credential. Examples of claims 472 may be the user DID 422, a registration number, an email address, a date of birth, and/or specific attributes associated with the credential issued to the user like a certification level or a number of educational credits earned.

Diagram 400 illustrates a VC with N number of claims 472, where N may be equal to one, two, four, six, et cetera. The proof(s) 482 are responsible for verifying the authenticity and ownership of the credential (i.e., the cryptographic signature of each relevant accreditation authority or certificate authority) such that the issuing authority (e.g., accreditation authority 158 or issuer 202) is verifying the user VC 442. Diagram 400 illustrates a single VC 442; however, multiple VCs 442 may be stored within a user cryptographic wallet 402. For example, an individual may have, inside their wallet, a first VC issued by their former academic institution verifying a degree, a second VC issued by an accreditation authority verifying a professional registration number associated with a certification, and a third VC issued by a government agency verifying the user's legal identity. Accordingly, users may store VCs 442 issued by the same or different authorities in their wallet 402.

User cryptographic wallet 402 can generate a VP (Verifiable Presentation) 444 from the user VC 442. The cryptographic wallet 402 also records the VP 444 in a VP log 492 for future auditability.

VP 444 contains one or more claims extracted from VC 442. VP 444 may contain multiple claims from different VCs with the same or different issuing authorities. VP 444 may contain all of the claims from a single VC or a portion of the claims. VP 444 can be cryptographically signed by the user before presenting the VP 444 to a verifier. VP 444 allows for minimum disclosure; hence, the user decides which claims 472 are or are not shared within the generated VP 444. In one example, the user is a pharmacist applying for a job and wants to show a potential employer proof of their degree (issued by a university), state licensure (issued by the state government), and proof of their legal identity (issued by a state or government agency). The user can choose to share one or more claims from each of these VCs to be presented as a VP towards the potential employer. In another example, the user is a Pharmacist interacting with a government auditor and wants to share all claims of the VC proving their licensure. When the entire VC is presented, it is still presented as a VP. In both examples, the information within the VP is easily verifiable because both (i) the user signature and (ii) the issuer signature are paired to respective DIDs that can easily be authenticated using the blockchain to which the DIDs are anchored.

Figure 5:
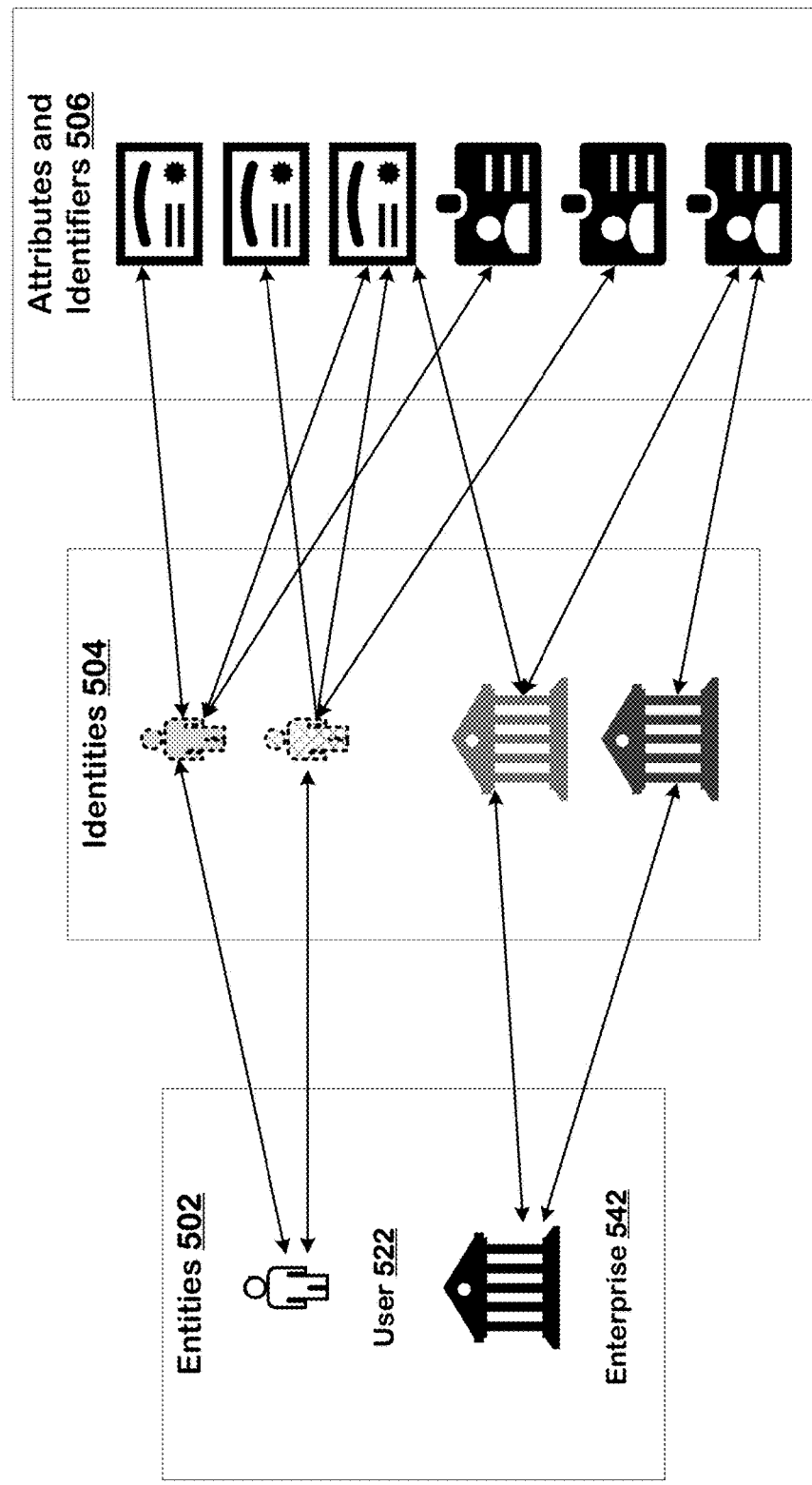
FIG. 5 shows a schematic illustrating a self-sovereign identity model, in accordance with one implementation of the technology disclosed.

FIG. 5 shows a schematic 500 illustrating a self-sovereign identity model, in accordance with one implementation of the technology disclosed. Thus far, the concept of the DID and VC have been presented in the context of the decentralized identity model 200, the triangle of trust model 300, and the presentation of a VC from a user cryptographic wallet in schematic 400. Accordingly, the description has focused on the authenticity, credibility, decentralized structure, and utility characteristics of leveraging VCs. Schematic 500 represents the self-sovereign identity characteristic of the DID and VC schema. Much like the models represented within 200, 300, and 400, schematic 500 is an example of certain particular implementations of the technology disclosed and is not relevant to other implementations.

One of the advantages of implementations that utilize variations on the VC model is that a user VC enables the credential holder to be sovereign in sharing the VC, and the credential verifier to be sovereign in validating the authenticity without consulting the issuer. Other approaches to digital identity may be disadvantageous in certain scenarios due to security risk (e.g., identifiers that are easily obtained or imitated), inconvenience (e.g., one user possessing a separate identifier for each respective registry in which they are enrolled), and barriers to verification (e.g., scenarios in which it is not possible to definitively verify the user, or verification is costly in terms of both time and monetary value). User authentication can often rely on methods that are poorly secured (e.g., password-based authentication, as previously described) or difficult to verify (e.g., identification cards that can be falsified or stolen). In contrast, the technology disclosed augments a link-based passwordless authentication approach with self-sovereign VCs such that the authentication is fast (in contrast to communication directly with the issuer or review of a physical proof of documentation), secure and tamper-proof, and enables users to maintain control over the information associated with their identity (in turn, removing the user's reliability on one or multiple identity providers). In certain implementations, the self-sovereign identity model is not feasible or compatible within an enterprise's existing infrastructure and the technology disclosed can leverage VCs and identities managed by a centralized schema. In other implementations, a self-sovereign model is leveraged.

In schematic 500, user 522 and enterprise 542 are entities 502 with respective identities. Most entities 502 can be represented as a variety of identities 504. User 522, for example, may have a first identity defined by legal identifiers (e.g., social security number) or a first set of attributes (e.g., date of birth and address) and a second identity defined by professional identifiers (e.g., licensure status and job title) or a second set of attributes (e.g., registration number or employee ID). Similarly, enterprise 542 may be defined by multiple identities differentiated by information directed towards tax purposes, licensure purposes, or authority status. Each respective identity 504 is defined by a set of attributes and identifiers 506, some of which may be overlapping between identities 504. In a traditional identity verification system, an entity 502 may need to manage separate digital identities for each identity 504 (each requiring unique registration for a service and enrollment of authentication factors for said service, and each potentially having control over verifying the identity), and furthermore, the entity 502 may not have an accessible method of verification for certain attributes of a credential at all. In certain scenarios, an enterprise's legacy channels rely on such an identity system and are not limited from utilizing the technology disclosed.

In contrast, utilization of a self-sovereign identity model within certain implementations of the technology disclosed allows users seeking to achieve bidirectional authentication by leveraging a messaging system/platform (such as email SMS, or other protocols), VCs, and secure web endpoints. It empowers a Sender to send a message enclosed with a VP which allows a Recipient to authenticate the message's provenance and the identity of the sender. Moreover, the message contains a link to a secure web endpoint, where the recipient can submit a response signed by their own VP, allowing the Sender to authenticate the identity of the Recipient, with neither participant required to have an account on the same service.

Additionally, the self-sovereign identity model provides a method of authenticating the content provenance of the transmitted messages between the Sender and User. Herein, provenance generally refers to a lineage of data ownership within a chain of messages. Historically, provenance has been complex to determine, especially in the context of centralized identity providers. For example, identity providers frequently authenticate the identity of users via a username and password combination and provide a limited set of attributes about the subject in the narrow context of the identity transaction. These identity providers are not interoperable, making it difficult to combine attributes across disparate registries. Accordingly, many such systems are configured to verify credentials on a fidelity level; i.e., verification of the digital identities of the Issuer and the Holder and verify that the credential has neither been tampered with or revoked. However, none of these verifications necessarily verify that the content and claims of the credential are legitimate.

Credential legitimacy ties back into the concept of the triangle of trust model 300, which explains that the verification of the Holder's credentials depends on the trust the Verifier places in the Issuer. If the Verifier trusts the Issuer, the Verifier may consequently trust the legitimacy of the credential. In other words, the cryptographic chain associated with the credential provides a form of credential provenance. The technology disclosed enables users to authenticate the provenance of a message in a manner that is cryptographically verifiable by means of leveraging a decentralized ledger (e.g., blockchain).

This approach addresses several fundamental weaknesses with messaging systems, such as email, SMS, and other legacy channels where spoofing and phishing are common. By anchoring authentication in VCs, it effectively represents a second authentication factor in addition to whatever trust participants might place in a communication route when sending to (or receiving from) a given messaging system (e.g., email) address. This is a superior means of two factor authentication than other channels such as SMS, as it can be entirely decentralized, and is less vulnerable to network attacks.

It is worth revisiting the previously introduced drawbacks to magic links and similar messaging system-backed (e.g., email-backed) passwordless authentication techniques. The limitations discussed (security is tied to the user's messaging system (e.g., email) account, users are able to share links, and vulnerability to man-in-the-middle attacks) are all addressed in that even if the messaging system (e.g., email) account is compromised, a bad actor still requires access to a relevant VC. (For instance, one might have access to a lawyer's messaging system (e.g., email) account, but they have no VC demonstrating a license to practice law.)

Moreover, the technology disclosed allows for authentication leveraging VCs on an open schema, therefore enabling interoperability between participants from disparate systems without demanding registration on centralized services or falling back on insecure and unreliable methods of information exchange.

Other, more direct methods exist for communication between holders of verifiable credentials, most notably, DIDcomm, a protocol for creating secure communication channels between software controlled by DID-controlling entities from diverse DID-based systems, which can be people, organizations or things. This constitutes an "authenticated channel," in that control of a given DID's private keys is (barring a failure of design or operational security) proof of authenticity of the party represented by that DID.

While DIDcomm is a mature protocol, adoption and integration into production systems remains in the early stages. To take advantage of VCs today, one must fall on more ad hoc approaches while recognizing the drawbacks until adoption has hit a point where DIDcomm is possible at scale. The technology disclosed provides a method to combine VCs with legacy channels to support.

The technology disclosed can further be implemented by sharing the VP for purposes of authentication, changing the method of integrating the VP with the message and/or using a standard that is similar to a VC, but not exactly the same (e.g., a more general or different cryptographic proof of identity).

Bidirectional Authentication Leveraging a Messaging System

FIG. 6A shows an architectural level schematic of a system component 600A for a user credentialing administration logic 152, in accordance with one implementation of the technology disclosed. User credentialing administration logic 152 is configured to provide a verifiable presentation of a received credential received from the user or a trusted identity authenticator on behalf of the user, the verifiable presentation including an electronic presentation of one or more instances of electronic evidence (a) personally identifying the user (e.g., the user's DID) and (b) supporting any credentialing issued to the user (e.g., proofs), or (c) a claim that the user is indeed associated with a digital endpoint from which the message originates for a sender user or to which the message is sent for a recipient user.

User credentialing administration logic 152 receives, as input, a Sender VC 602 for a Sender seeking to send a message originating at a first digital endpoint, and provides, as output, a Sender VP 604 that includes electronic evidence of the sender user's credentials that are associated with the particular Sender's message and/or function of said message (see FIG. 8 for an example implementation illustrating the relationship between the credentials of the Sender/Recipient and the function of the message). Accordingly, user credentialing administration logic 152 receives, as input, a Recipient VC 624 for a Sender seeking to send a message originating at a first digital endpoint, and provides, as output, a Recipient VP 622 that includes electronic evidence of the recipient user's credentials. VPs 604 and 622 may then be included within the messaging facilitated by message exchange logic 154, described below with reference to FIG. 6B.

FIG. 6B shows an architectural level schematic of a system component 600B for a message exchange logic 154, in accordance with one implementation of the technology disclosed. Message exchange logic 154 is configured to generate a link containing query parameters uniquely identifying a message, verify the VP of the Sender of the message, and provide the link to the Recipient that directs the Recipient to a web portal with a response form in response to the Sender message. Message exchange logic 154 receives a Recipient VP and verifies the Recipient, then allows the Recipient access to the Sender message. Thus, in transmitting the Sender message and Recipient response message, both users are authenticated in the process and the Recipient is able to access the link in a passwordless manner.

Message exchange logic 154 receives the Sender message 642 as input, wherein the Sender message 642 includes the message content 622 and the Recipient digital endpoint 623, directing the message. If the Sender VP 625 is verifiable, the message exchange logic 164 generates Sender message 642, now containing the message content 622, Recipient digital endpoint 623, a one-time-use link 624, and a signature containing the Sender DID and VP 625. Link 624 further includes the Sender DID, the UUID of the Sender VP, and authentication information (expanded upon in further detail within FIGS. 13-19).

On behalf of the Recipient, the message exchange logic 164 verifies the Sender VP 625 and, if verifiable, sends Sender message 642 to the Recipient digital endpoint (e.g., email), thereby providing the Recipient access to link 624. Link 624 directs the Recipient to a web portal (e.g., web portal 167) and receives, via the web portal, the Recipient VP 675. If verifiable, the Recipient is provided access to the message content 622 and may respond accordingly (e.g., filling out a form and sending the form back to the Sender). The Recipient response message 664, containing the response content 672 and the Sender digital endpoint 673, directing the message. Message exchange logic 154 notifies the Sender of the response via the web portal, and the Sender can access the response message 662, which has been signed by the Recipient VP 674.

Figure 7:
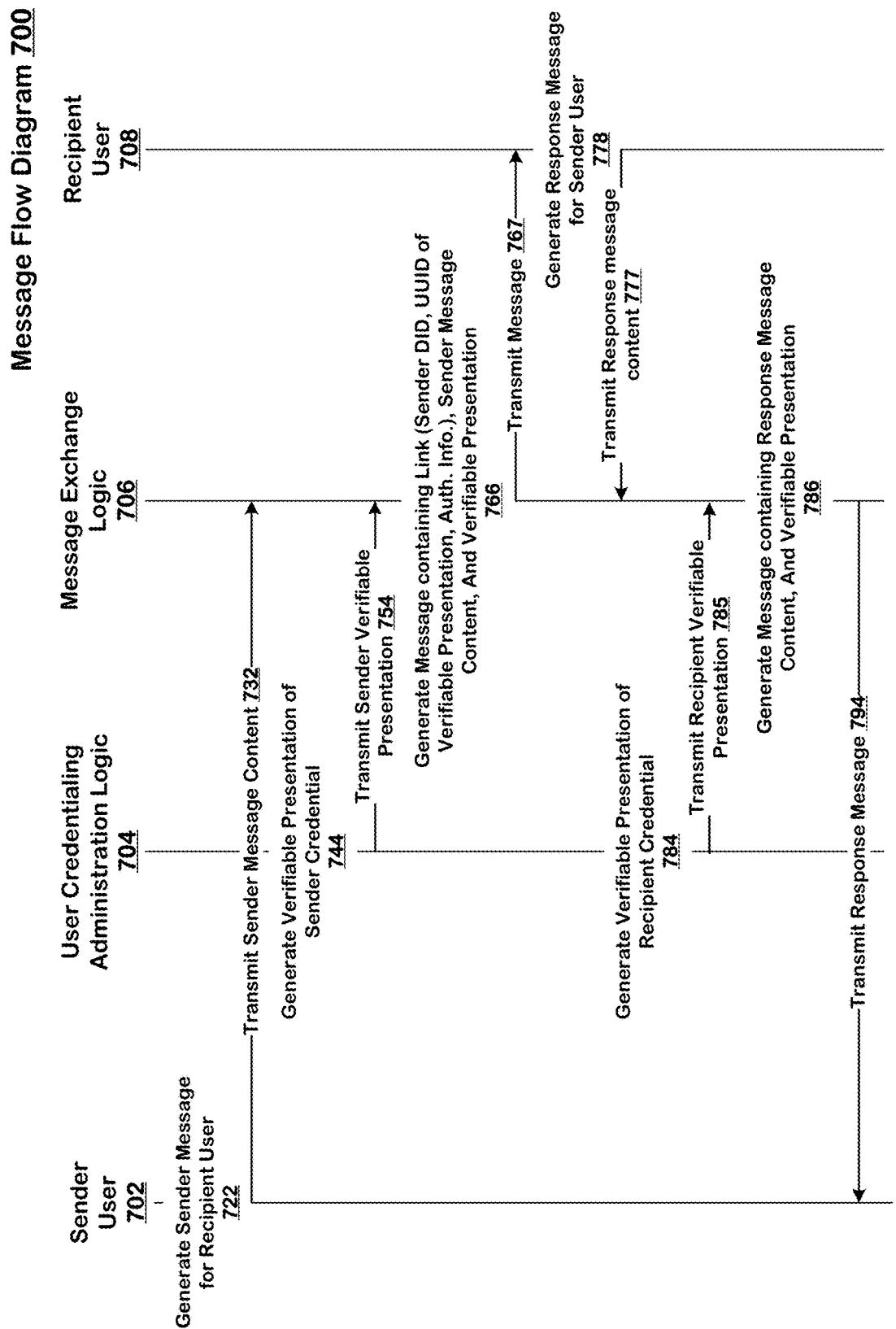
FIG. 7 is a message flow diagram illustrating bidirectional authentication between two actors leveraging a messaging system.

FIG. 7 is a message flow diagram 700 illustrating bidirectional authentication between two actors 702 and 708 leveraging a messaging system. In operation 722, a Sender user 702 generates a Sender message for a Recipient user 708. The Sender message content is transmitted to message exchange logic 708 in operation 732. Additionally, user credentialing administration logic 704 generates a VP of the Sender VC in operation 744, which is also provided to the message exchange logic 706 in an operation 754. The message exchange logic 706, in operation 766, generates the Sender message containing a one-time-use link, the Sender message content, and the Sender VP (which has been verified by the message exchange logic 706). The message is provided to Recipient user 708 in an operation 767, thereby providing the Recipient user 708 with the one-time-use link in order to access the message and respond. In operation 778, Recipient user 708 generates the Recipient response message for the Sender user 702.

The Recipient response message content is transmitted back to the message exchange logic 706 in operation 777, and user credentialing administration logic 704 generates a VP of the Recipient VC in operation 784. In operation 785, the Recipient VP is transmitted to the message exchange logic 706, and if verifiable, the message exchange logic 706 generates the response message containing the message content and a signature consisting of the Recipient VP in operation 786. Next, the Sender user 702 is notified of the response message in operation 784.

An example is provided next with reference to FIG. 8 for illustrative purposes, in accordance with one implementation of the technology disclosed.

FIG. 8 shows a schematic 800 illustrating an example implementation for the technology disclosed. Schematic 800 describes a workflow in accordance with one implementation of the technology disclosed; particularly, with regards to the description above in reference to FIGS. 6A, 6B, and 7.

The illustrated workflow involves Alice 801, a government inspector, and Charlie 821, a drug wholesaler, in which Alice 801 is requesting information to be provided by Charlie 821. In this scenario, Alice 801 was provided with Charlie's email address 837 by Bob the Pharmacist to facilitate communication between Alice 801 and Charlie 821. Alice 801 and Charlie 821 have no prior knowledge of each other. Alice 801 has a VC 822 and Charlie has a VC 823, but they do not use any other services in common; i.e., they are not enrolled in a common centralized identity provider's registry.

Alice 801 has a cryptographic wallet 802 accessible to a device (e.g., a client device 122 such as a tablet or smart phone) on which her DID 812, VC 822, and a log of any VPs 852 are stored. Alice's VC 822 contains a combination of various metadata and claims 832 demonstrating her credentials as a Government Inspector, and the VC 822 is signed with the accreditation authority's cryptographic signature 842 for authenticity and verification purposes. VP 804 can be generated for Alice's VC 822 to present her credentials as an inspector to a requesting Verifier. User credentialing logic 152 can receive Alice's VC 822 (i.e., from Alice 801 or from an identity authenticator on behalf of Alice 801) and provide VP 804, including an electronic presentation of evidence identifying Alice 801, as well as one or more claim(s) and/or proof(s) that support her credentialing as a Government Inspector 832 and verify that Alice 801 is indeed associated with a digital endpoint from which Alice 801 sends any messages. Hence, VP 804 enables Alice 801 to be able to send an authenticated message to Charlie 821 supported by her VC 822.

Similarly, Charlie 821 has a cryptographic wallet 803 accessible to a device (e.g., a client device 122 such as a tablet or smart phone) on which his DID 813, VC 823, and a log of any VPs 853 are stored. Charlie's VC 823 contains a combination of various metadata and claims 833 demonstrating his credentials as a Drug Wholesaler, and the VC 823 is signed with the accreditation authority's cryptographic signature 843 for authenticity and verification purposes. VP 844 can be generated for Charlie's VC 823 to present his credentials as an inspector to a requesting Verifier. User credentialing logic 152 can receive Charlie's VC 823 (i.e., from Charlie 821 or from an identity authenticator on behalf of Charlie 821) and provide VP 844, including an electronic presentation of evidence identifying Charlie 821, as well as one or more claim(s) and/or proof(s) that support his credentialing as a Drug Wholesaler 833 and verify that Charlie 821 is indeed associated with a digital endpoint from which Charlie 821 sends any messages. Hence, VP 804 enables Charlie 821 to be able to send an authenticated response to a message from Alice 801 supported by his VC 823.

In operation 806, Alice 801 logs into a secure website which has access to her cryptographic wallet 802, including her VC 822 establishing her status as a Government Inspector 832. She fills out a form requesting information from Charlie 821, accessible to a server 816. Server 816 includes, or is otherwise associated with, user credentialing administration logic 152 and message exchange logic 154. Thus, for simplicity, schematic 800 cumulatively represents the operations performed by user credentialing administration logic 152 and message exchange logic 154 as being performed by server 816. Server 816 receives Alice's request form 826 and signs her request with a W3C-compliant VP 804 (accessible either via Alice's cryptographic wallet 802 or, if the website does not have permission to access wallet 802, another route mediated by Alice 801 such as transferring the VP 804 from another service). Alice's full message 836 comprises her request 846, VP 804, and a one-time-use link 866 that enables Charlie 821 to interact with Alice's request 846.

In operation 807, server 816 sends Alice's message 836 to Charlie 821 via the digital endpoint identified by Alice 801, i.e., Charlie's email address 837. In this example, Alice 801 is the Sender user/Holder user and Charlie 821 is the Recipient user/Verifier user. Hence, in operation 808, Charlie 821 receives the email containing Alice's message 836. Message 836 contains the request 846, Alice's VP 804, and one-time link 866. Attached to the email are files describing the request 846 (e.g., JSON, CSV, etc.) and the body of the email includes a plaintext description of the request 846. The link 866 contains query parameters uniquely identifying the message, including Alice's DID 812, a UUID of her VP 804, and additional authentication data. Assuming that Alice's VP 804 is verifiable by server 816, Charlie 821 is able to access link 866 via the email.

In operation 808, Charlie 821 clicks on the link 866, which directs him to a secure web endpoint with a fillable form. From here, in operation 809, Charlie 821 can fill response form 829 to respond to request 846. The final response message 839 can be signed with Charlie's W3C-compliant VP 844, of which is either obtained directly via Charlie's cryptographic wallet 803 or copied and pasted in by Charlie 821, thereby providing an additional level of assurance about his identity. In operation 810, server 816 receives Charlie's submitted and signed form 839 following his submission and notifies Alice 801 of the response. This can include updating a web dashboard for Alice 801 to show that a response has been submitted, or alternatively/in addition to updating her web dashboard, sending an email message to Alice 801. Optionally, operation 811 can be performed such that the server 816 also sends a record of the response via carbon copy 859 to Charlie 821. To further aid in the illustration of this scenario, FIGS. 9-12 show example presentations via a client display operating within a client device of a GUI within the secure web interface used by Alice 801 and Charlie 821.

Figure 9:
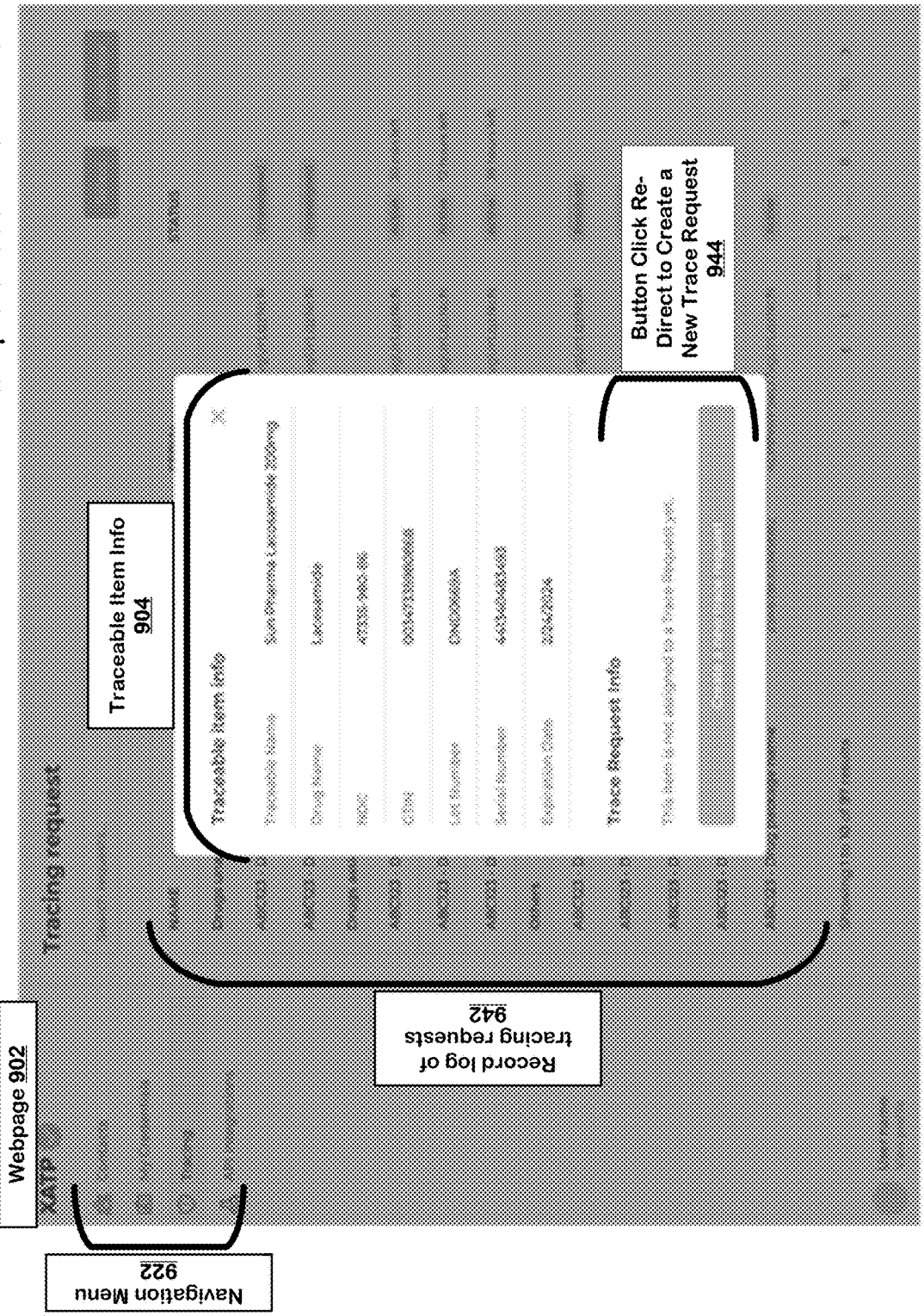
FIG. 9 is an example of a GUI for a secure web interface that allows for a sender user to send a message enclosed with a Verifiable Presentation to a recipient user.

FIG. 9 is an example of a GUI 900 for a secure web interface that allows for a sender user to send a message enclosed with a Verifiable Presentation to a recipient user. GUI 900 displays towards the user a webpage 902 within the secure web portal domain in which the Sender, e.g., Alice 801, intends to submit a request message. Within navigation menu 922, the Sender may navigate towards a list of contacts, review their credentials, access a record log of inventory tracing requests, and access API integrations. Webpage 902 currently accessed by the Sender is a record log of tracing requests 942, as illustrated in the background of a pop-up box. The pop-up box includes traceable item info 904. Continuing with the example introduced in schematic 800, Alice 801 is able to create a new trace request and transmit this trace request to Charlie 821, via a button-click 944 that re-directs Alice 801 towards webpage 1002 to create a new trace request, for a particular formulation of a drug Lacosamide.

Figure 10:
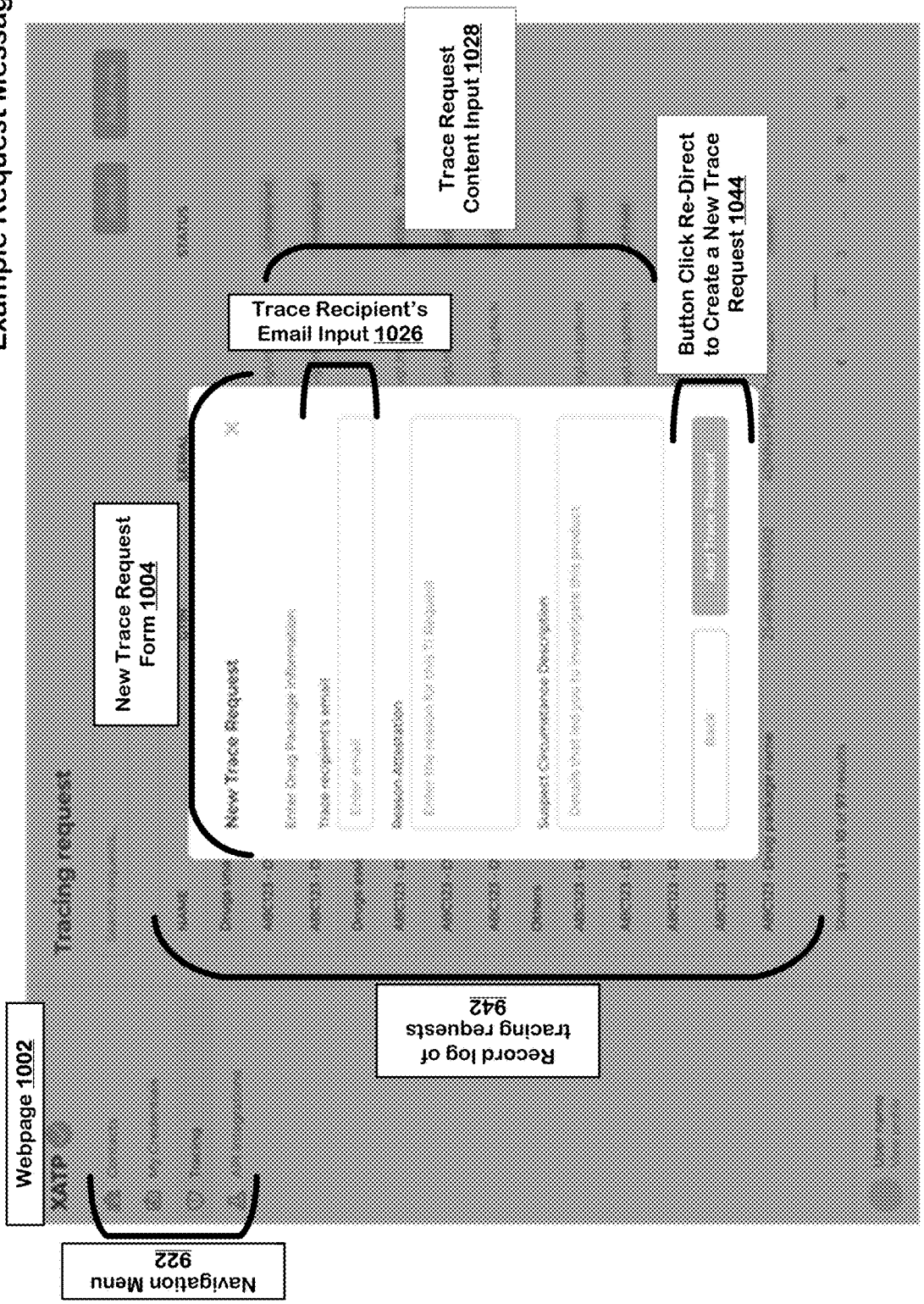
FIG. 10 is an example of a GUI for a secure web interface that allows for a sender user to generate a message enclosed with a Verifiable Presentation to a recipient user.

FIG. 10 is an example of a GUI 1000 for a secure web interface that allows for a sender user to generate a message enclosed with a Verifiable Presentation to a recipient user. GUI 1000 displays webpage 1002 within the secure web portal domain that Alice 801 is using to submit a drug tracing request for Charlie 821 during an audit. Similarly to webpage 902, webpage 1002 displays a navigation menu 922 and record log of tracing request 942 in the background of a pop-up message. Following Alice's input via selecting button click re-direct 944, the pop-up now displays a fillable form for a new trace request 1028. Alice 801 may provide inputs for the content of the trace request 1028 (i.e., tracing audit for the particular Lacosamide formulation) and specify an email address 837 for Charlie 821 as input 1026 to direct the message towards the appropriate digital endpoint. After Alice 801 is finished generating her request, she is able to create the request via a button-click 1044, thereby submitting the trace request so that it is sent to Charlie 821. Once Alice 801 submits the trace request, the secure web portal signs the request with Alice's VP 804 and sends the signed request along to Charlie 821 along with a one-time use link 866 that directs him to webpage 1102.

FIG. 11 is an example of a GUI 1100 for a secure web interface that allows for a recipient user to generate a response message to be transmitted back to a sender user. GUI 1100 displays webpage 1102 within the secure web portal domain, accessed by Charlie 821 using link 866. Webpage 1102 presents the content of Alice's tracing request 1104 to Charlie 821, including a summary 1128 of the Requestor's, i.e., Alice's, information and the request content. Charlie can trust the authenticity of the request, and the identity of Alice 801, because the secure web portal server has verified Alice's VP 804. Charlie 821 is able to submit a tracing response via a button-click 1144, redirecting Charlie 821 to a fillable response form. Once Charlie fills the response form, the secure web portal signs the response with Charlie's VP 844 prior to notifying Alice 801 of the new response. Thus, Alice 801 is also able to trust the authenticity of the response, and the identity of Charlie 821, because the web portal server has verified Charlie's VP 844.

FIG. 12 is an example of a GUI 1200 for a secure web interface displaying a carbon copy of a response message for the recipient user. In addition to notifying Alice 801 of the response, Charlie 821 is also able to access webpage 1202 via the secure web portal. Webpage 1202 presents a carbon copy of the tracing response 1204 including the content of the tracing response content 1228.

The description of the above-referenced figures has primarily focused on the Verifiable Credentialing of the Sender and Recipient users in bidirectional authentication. Another aspect of the technology disclosed, in accordance with particular implementations, is the authentication of the content provenance of a message. The query parameters uniquely identifying the message include, along with the Sender DID and UUID of the Sender VP, authentication information for the message. This authentication information can comprise a reference to a hash-addressable, hash-verifiable chained data structure resident referred to as a "plum" in a data cache that stores content provenance for the message. Each plum includes (i) a head and a head seal comprising a hash value of the head, (ii) metadata and a metadata seal comprising a hash value of the metadata, (iii) one or more relations and a relations seal comprising a hash value of the relations, and (iv) a body and a body seal comprising a hash value of the body. For each message version created and signed using a verified signature of the Sender user, a new plum is added to the data cache and chained to an ancestor of a prior message version forming a chain of plums. The description now turns to focus on the plum and chain of plums.

Message Content Provenance Authentication

Figure 13:
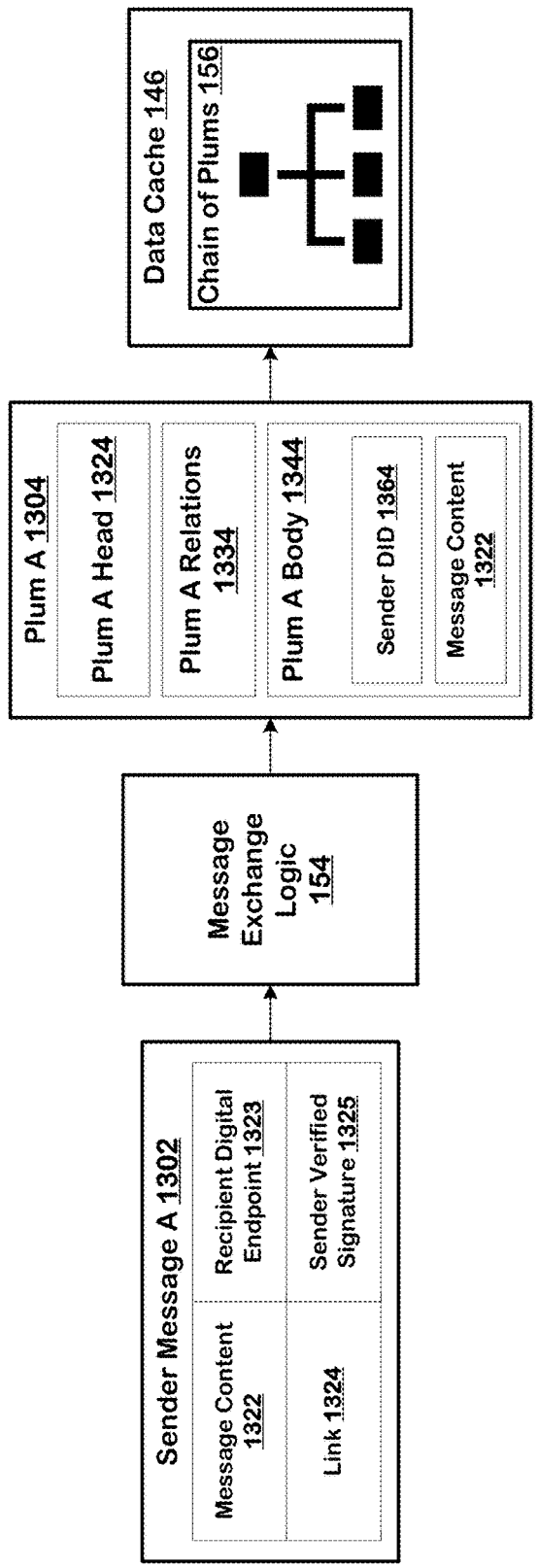
FIG. 13 is a simplified block diagram of a message exchange logic instantiating a plum for a sender message to be stored within a chain of plums in a data cache, in accordance with one implementation of the technology disclosed.

FIG. 13 is a simplified block diagram 1300 of a message exchange logic 154 instantiating a plum A 1304 for a sender message A 1302 to be stored within a chain of plums 156 in a data cache 146, in accordance with one implementation of the technology disclosed.

When the message exchange logic 154 is sending a message 1302 on behalf of the Sender user, the logic is configured to prompt the sender user for their verified signature 1325 (i.e., the Sender DID and VP) and message content 1322, followed by instantiating a plum A 1304 corresponding to the message A 1302. Plum A 1304 includes a head 1324, relations 1334, and body 1344. Plum A 1304 can also include metadata, not shown in diagram 1300 for simplicity. The message exchange logic 154 then incorporates the message content 1322 and the DID of the Sender user 1364 into a body 1344 of the plum 1304, computes a body seal hash of the body, computes a head seal hash value for the plum and adds the plum to the data cache 146. The plum can additionally maintain a time stamp for each validation of a verified signature. The structure of a plum is further described with reference to FIG. 14. When adding a new version of the Sender message 1302, the message exchange logic 154 is configured to instantiate a child plum, populate the body with new version message content and verified signature of the sender user, incorporate relation information of the plum as a parent plum, compute a body seal hash of the body, a relations seal hash value of the relation information, and a head seal hash value for the child plum and add the child plum to the data cache 146, in which the child plum is chained to the parent plum within the chain of plums 156.

The message exchange logic 154 is also configured to authenticate the content provenance of a message version via iterating through the chain of plums 156 until a plum corresponding to the message version is reached. This may also apply to the authentication of content provenance for multiple message versions, in which the message exchange logic 154 iterates through the chain of plums 156 until reaching the corresponding plums for the multiple message versions. When the message exchange logic 154 is authenticating the content provenance of a received message on behalf of the Recipient user 1323, logic 154 is configured to iterate through the chain of plums 156 beginning with an ancestral plum and until a plum(s) corresponding to a message version(s) whose content provenance is to be authenticated is/are reached, and for each plum in the chain of plums 156 verify matching corresponding data entries for (a) a nonce, (b) a subject, (c) ancestral relationship, and (d) a verified signature, and verify concordance with other plums in the chain of plums 156 of owned data for the plum including: (x) the decentralized identifier, (y) additional metadata, and (z) previous owned data.

Moreover, it is possible to track the evolution of a message across sequential versions by tracking a difference between metadata and content of an $n^{th}$ version and the metadata and content of an $n-1^{th}$ version. The structure and content of a plum will now be explained in further detail.

Figure 14:
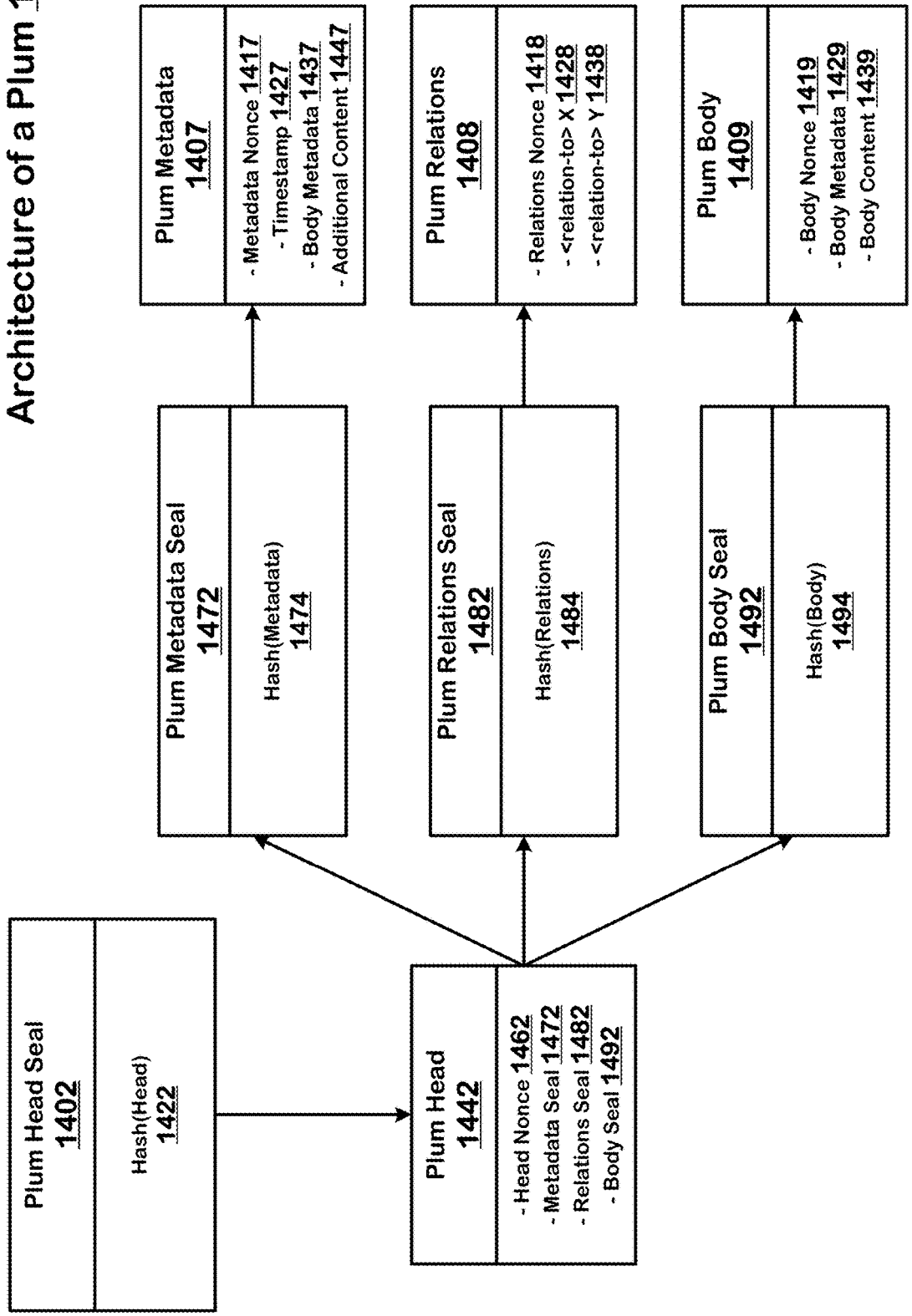
FIG. 14 shows a schematic illustrating the architecture of a plum, in accordance with one implementation of the technology disclosed.

FIG. 14 shows a schematic 1400 illustrating the architecture of a plum, in accordance with one implementation of the technology disclosed.

The technology disclosed comprises a plum, the architecture of which is illustrated within schematic 1400, wherein the plum may be associated in various implementations with cryptographic concepts such as hash functions, nonce values, Merkle trees, and deduplication. Schematic 1400 comprises a plum head seal 1402, a plum head 1442, a plum metadata seal 1472, plum metadata 1407, a plum relations seal 1482, plum relations 1408, a plum body seal 1492, and a plumb body 1409. The components of schematic 1400 are understood to be non-limiting in scope and representative of one implementation of the technology disclosed. Other data fields and associated components that may be present in additional implementations are not shown in FIG. 14 for clarity. Plum head seal 1402 further comprises the hash value Hash(Head) 1422 for the plum head 1442. Hash(Head) 1422 and all additional hash values discussed herein can be considered to be generated from a plurality of hash functions, and a user of ordinary skill in the art will be familiar with the various functions that may be implemented within the technology disclosed.

Plum head 1442 is further associated with a head nonce value 1462, a metadata seal 1472, a relations seal 1482, and a body seal 1492. Plum metadata seal 1472 further comprises a hash value Hash(Metadata) 1474 associated with plum metadata 1407, such as a metadata nonce value 1417, a timestamp 1427, body metadata 1437, and additional content 1447. Plum relations seal 1482 further comprises a hash value Hash(Relations) 1484 associated with plum relations 1408. Plum relations 1408 may be further associated with values for a relations nonce 1418, a <relation-to> X entry 1428, and a <relation-to> Y entry 1438 wherein X and Y are related plums to the plum represented by schematic 1400. Plum body seal 1492 further comprises a hash value Hash(Body) 1494 associated with plum body 1409.

The plum body 1409 may be further associated with values for a body nonce 1419, body metadata 1429, and body content 1439.

Example pseudocode for a plum data structure, in accordance with some implementations of the technology disclosed, is provided below, in which the head and relations data are published.

Head
Head Nonce: None
Metadata Seal: Hash(Metadata)
Relations Seal: Hash(Relations)
Body Seal: Hash(Body)
Metadata
Metadata Nonce: MetadataNonceValue
Plum Created At: Time Stamp
Body Content Length: LengthValue
Body Content Class: text/plain
Body Content Format: FormatType
Body Content Encoding: EncodingType
Relations
Relations Nonce: RelationsNonceValue
Relations Entries (n in Total): Entry 1, . . . , Entry n
Body
Body Nonce: Nonce Value
Body Content Length: LengthValue
Body Content Class: text/plain
Body Content Format: FormatType
Body Content Encoding: EncodingType
Body Content Follows
BodyContentText Additional example pseudocode for a plum data structure, in accordance with another implementation, is provided below, in which the owner must sign each update.

Figure 15:
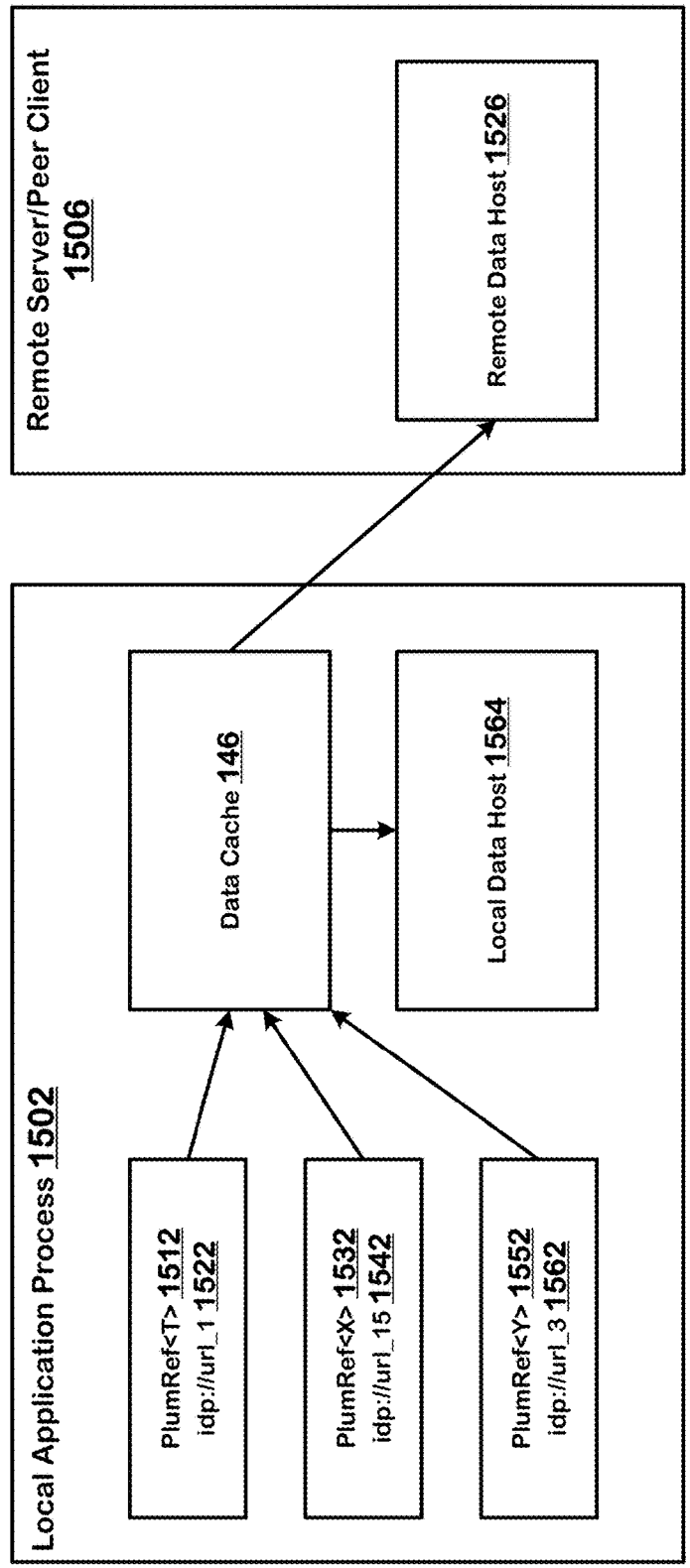
FIG. 15 shows a schematic illustrating a transparent reference type for a plum, in accordance with one implementation of the technology disclosed.

Head
Head Nonce: None
Metadata Seal: Hash(Metadata)
Relations Seal: Hash(Relations)
Body Seal: Hash(Body)
Metadata
Metadata Nonce: MetadataNonceValue
Plum Created At: Time Stamp
Body Content Length: LengthValue
Body Content Class: text/plain
Body Content Format: PlumSig
Body Content Encoding: EncodingType
Relations
Relations Nonce: RelationsNonceValue
Relations Entries (1 in Total): Entry 1
Content Previous Owner: PreviousOwnerValue
Body
Body Nonce: BodyNonceValue
Body Content Length: LengthValue
Body Content Class: text/plain
Body Content Format: PlumSig
Body Content Encoding: EncodingType
Body Content Follows
Nonce: SigNonceValue
Content Previous Owner: PreviousOwnerValue
Content Previous Verified Signature: PreviousSig
Signature: PlumSignatureValue
Signature Is Valid FIG. 15 shows a schematic 1500 illustrating a transparent reference for a plum, in accordance with one implementation of the technology disclosed. A local application process 1502 comprises a plum reference variable PlumRef<T> 1512, associated respectively with a first particular URL idp://url_1 1522, a plum reference variable PlumRef<X> 1532, associated respectively with a second particular URL idp://url_2 1542, and a plum reference variable PlumRef<Y> 1552, associated respectively with a third particular URL idp://url_1 1562. Each respective URL 1522, 1542, and 1562 is a URL pointer to the particular associated plum within data cache 146, accessible via the local data host 1564. In some implementations, data cache 146 is also accessible to a remote data host 1526 housed on a remote server/peer client 1506.

Figure 16:
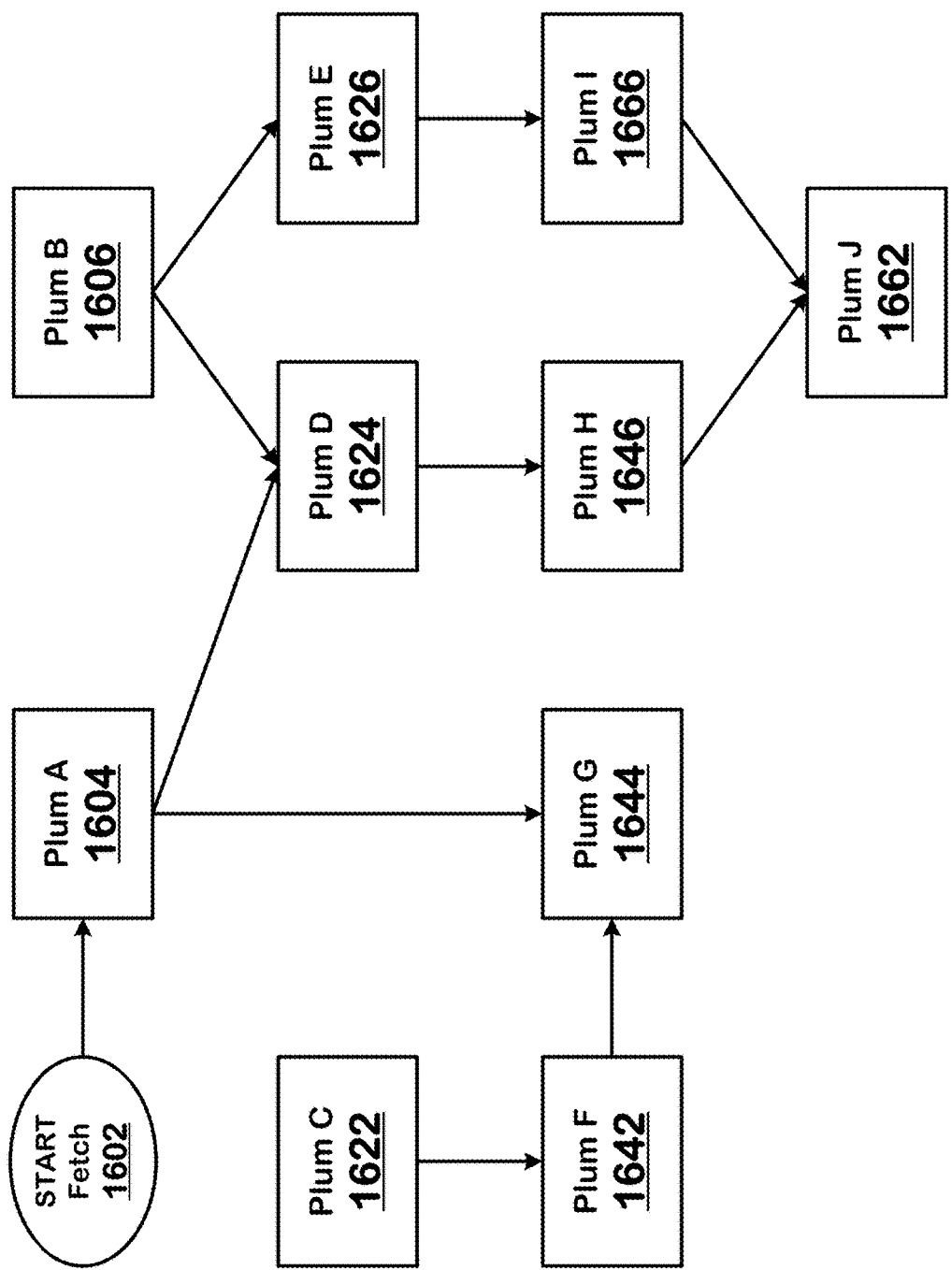
FIG. 16 is a simplified block diagram of a dependency graph within a chain of plums.

FIG. 16 is a simplified block diagram of a dependency graph 1600 within a chain of plums 156. To fetch the proper plum, message exchange logic 156 may begin the function at operation 1602 and continue iterating through the chain of plums until the desired plum(s) is/are reached. For example, Plum A 1604 is an ancestor of Plum G 1644. Plum C 1622 is an ancestor of Plum F 1642, and Plum F 1642 is an ancestor of Plum G 1644. Plum B 1606 is an ancestor of both Plum D 1624 and Plum E 1626. Plum D 1624 is an ancestor of Plum H 1646 and Plum E 1626 is an ancestor of Plum I 1666. Plum H 1646 and Plum I 1666 are both ancestors of Plum J 1662. As illustrated by diagram 1600, more than one plum may be an ancestor of a child plum without the ancestor plums themselves being directly related. For example, Plum J 1662 is related to both Plum A 1604 and Plum E 1626, but there is not a direct relationship between Plum A 1604 and Plum E 1626. The difference in metadata can be tracked by the message exchange logic 156 between plums within a chain of related plums.

Figure 17:
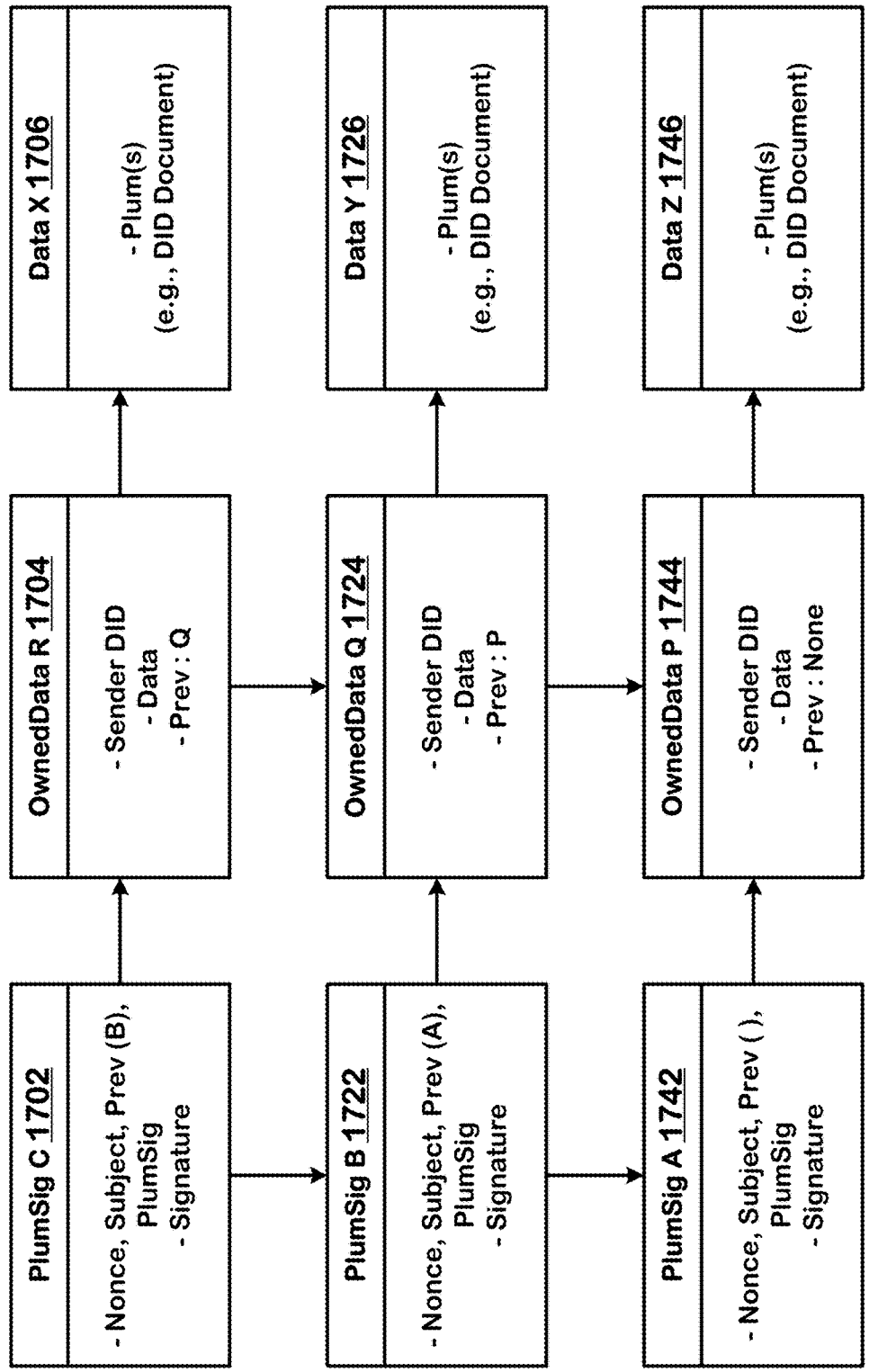
FIG. 17 is a simplified block diagram of message content provenance authentication leveraging a chain of plums.

FIG. 17 is a simplified block diagram 1700 of message content provenance authentication leveraging a chain of plums 156, in accordance with one implementation of the technology disclosed. Diagram 1700 illustrates three related plums: Plum A, Plum B, and Plum C such that Plum A is the parent to Plum B and Plum B is the parent to Plum C.

PlumSigC 1702 is associated with values respective to Plum C such as a nonce, a subject, the ancestral relationship to Plum B, and a verified signature. PlumSigC 1702 is further associated with OwnedData R 1704, such as an Sender DID, additional metadata, and previous owned data (OwnedData Q 1724) associated with the parent Plum B. Data X 1706 associated with OwnedData R 1704 may include one or more plum(s) such as a Sender DID document. PlumSigC 1702 is linked to PlumSigB 1722, and PlumSigB 1722 is associated with values respective to Plum B such as a nonce, a subject, the ancestral relationship to Plum A, and a verified signature. PlumSigB 1722 is further associated with OwnedData Q 1724, such as an Sender DID, additional metadata, and previous owned data (OwnedData P 1744) associated with the parent Plum A. Data Y 1726 associated with OwnedData Q 1724 may include one or more plum(s) such as a DID document. PlumSigB 1722 is linked to PlumSigA 1742, and PlumSigA 1742 is associated with values respective to Plum A such as a nonce, a subject, any ancestral relationships to Plum A (within this example, there are no ancestors to Plum A), and a verified signature. PlumSigA 1742 is further associated with OwnedData P 1744, such as an Sender DID or additional metadata. Plum A has no linked ancestors; thus, there is no previous owned data associated with the parent Plum A. Data Z 1746 associated with OwnedData P 1744 may include one or more plum(s) such as a DID document. As a result of the inherent relationship between Plums A, B, and C, the ancestral linkage between the three plums is also reflected within the associations of OwnedData R 1722, OwnedData Q 1724, and OwnedData P 1744.

Third example pseudocode for a data structure associated with the technology is given below, wherein the owner signature, i.e., the verified signature of the Sender, has been validated.

Plum: PlumIDValue
Head
Head Nonce: None
Metadata Seal: Hash(Metadata)
Relations Seal: Hash(Relations)
Body Seal: Hash(Body)
Metadata
Metadata Nonce: MetadataNonceValue
Plum Created At: Time Stamp
Body Content Length: LengthValue
Body Content Class: BranchNode
Body Content Format: json
Body Content Encoding: EncodingType
Relations
Relations Nonce: RelationsNonceValue
Relations Entries (3 in Total): CONTENT_DEPENDENCY:
ContentDependencyEntry, METADATA_DEPENDENCY:
MetadataDependencyEntry1, METADATA_DEPENDENCY:
MetadataDependencyEntry2
Body
Body Nonce: BodyNonceValue
Body Content Length: LengthValue
Body Content Class: BranchNode
Body Content Format: json
Body Content Encoding: EncodingType
Body Content Follows
Ancestor DataValue(s): AncestorNonceValue AncestorContentClass
AncestorContentFormat Content Preview: AncestorContentValue
Content Previous Verified Signature: PreviousSig
Metadata: MetadataNonceValue1 AncestorContentClass1
AncestorContentFormat1 Content Preview: AncestorMetadataContentValue1
Metadata: MetadataNonceValue2 AncestorContentClass2
AncestorContentFormat2 Content Preview: AncestorMetadataContentValue2

Figure 18:
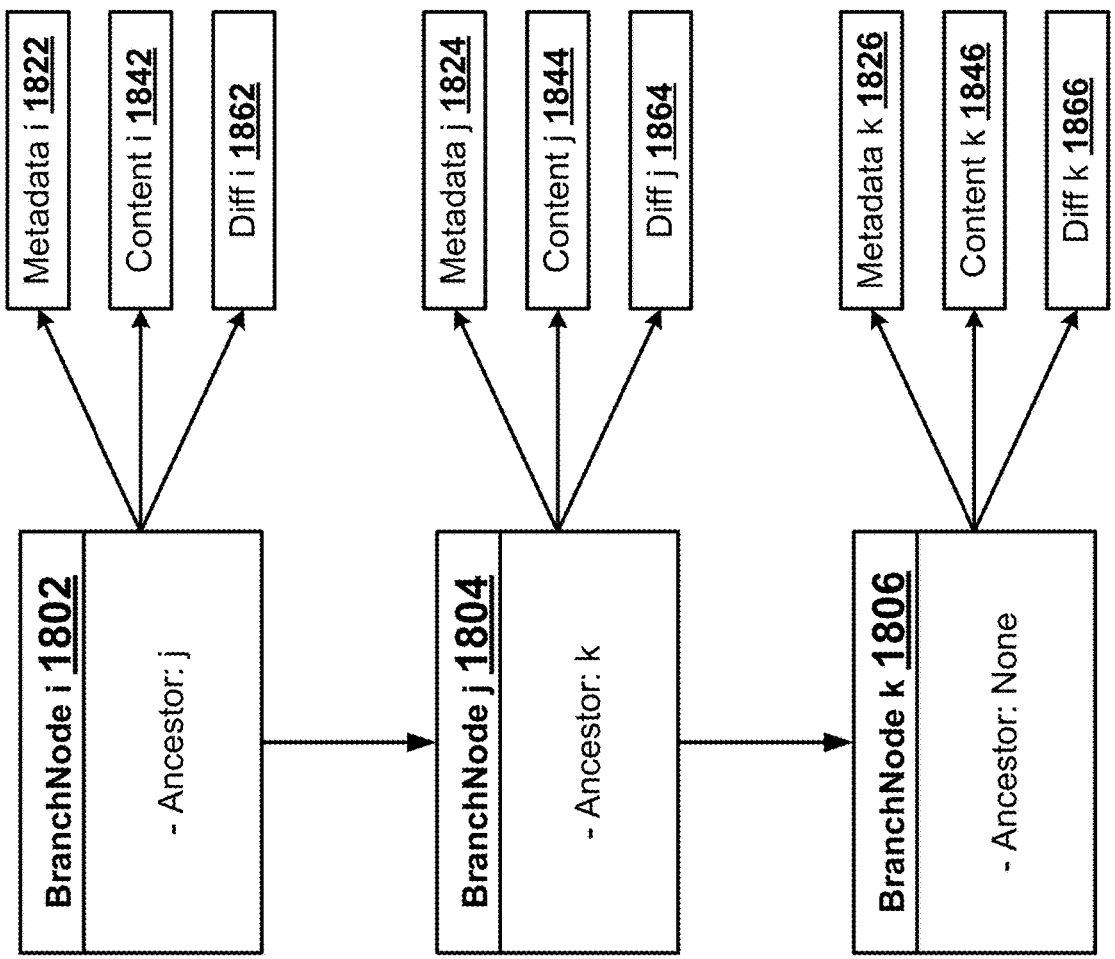
FIG. 18 is a simplified block diagram of related parent and child plums corresponding to message versions within a chain of plums.

FIG. 18 is a simplified block diagram 1800 of related parent and child plums corresponding to message versions within a chain of plums 1186, in accordance with one implementation of the technology disclosed. A BranchNode i 1802 is a child of a BranchNode j 1804, which is a child of BranchNode k 1806. The revisions to the content within the branch nodes are recorded as a versioning feature. For example, BranchNode k 1806 has associated Metadata k 1826, Content k 1846, and Diff k 1866. BranchNode j 1804 has associated Metadata j 1824, Content j 1844, and Diff j 1864, which can be contrasted to the respective values of Metadata k 1826, Content k 1846, and Diff k 1866 associated with the ancestor node, BranchNode k 1806. BranchNode i 1802 has associated Metadata i 1822, Content i 1842, and Diff i 1862, which can be contrasted to both the respective values of Metadata j 1824, Content j 1844, and Diff j 1864 associated with the ancestor node, BranchNode j 1804 and the respective values of Metadata k 1826, Content k 1846, and Diff k 1866 associated with the ancestor node, BranchNode k 1806.

Figure 19:
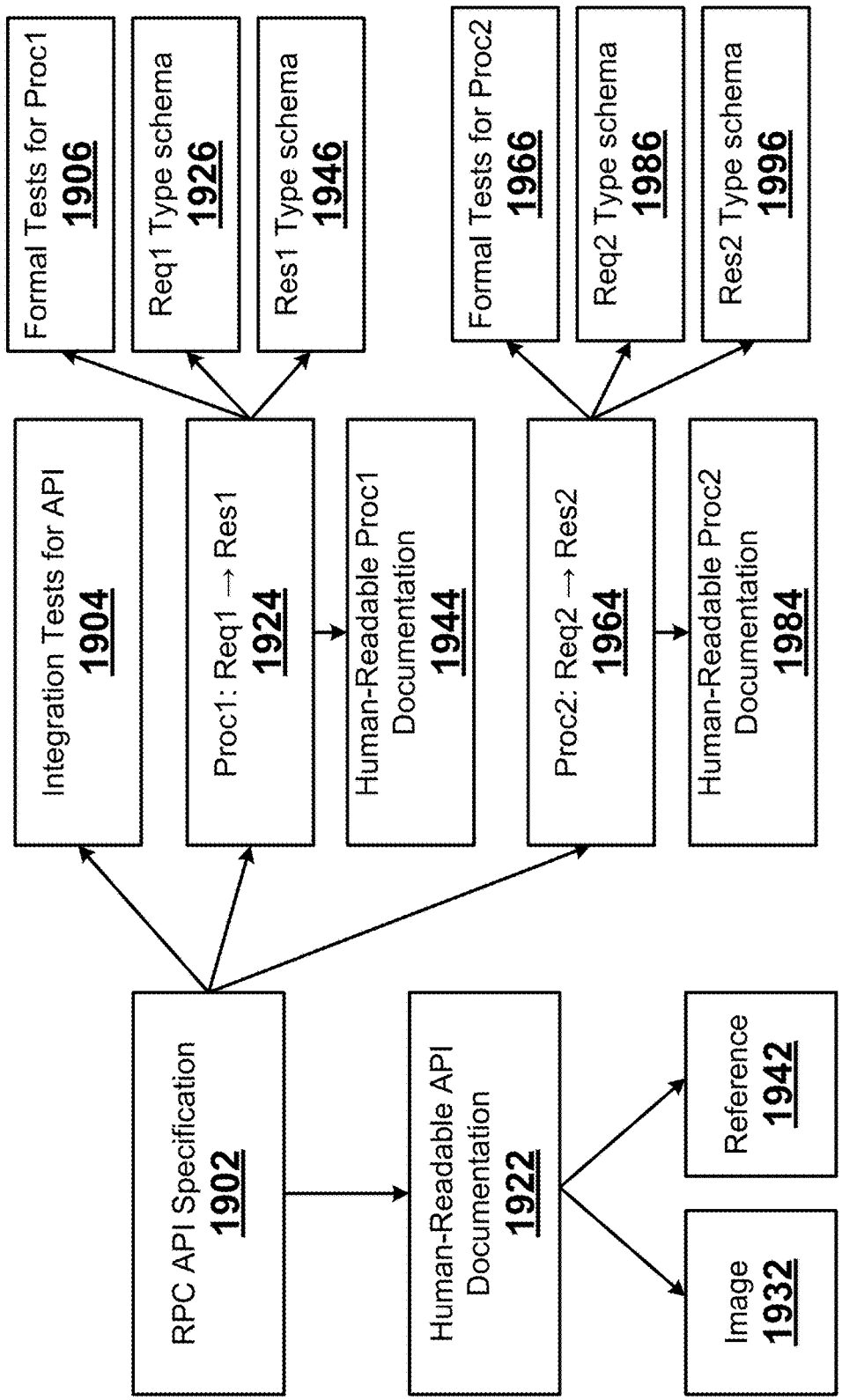
FIG. 19 shows a schematic illustrating an example type schema to define an RPC API specification, in accordance with one implementation of the technology disclosed

FIG. 19 shows a schematic 1900 illustrating an example type schema to define an RPC API specification, in accordance with one implementation of the technology disclosed. RPC API Specification 1902 can be converted into human-readable API documentation 1922, containing at least an image 1932 and a reference 1942. The RPC API Specification 1902 may be associated with integration tests for the respective API 1904, a first process (Proc1) 1924 comprising a first request (Req1) and a first result (Res2), and a second process (Proc2) 1964 comprising a second request (Req2) and a second result (Res2). Proc1 1924 is further associated with formal tests 1906 for Proc1, a Req1 type schema 1926, and a Res1 type schema 1946. Likewise, Proc2 1964 is further associated with formal tests 1966 for Proc2, a Req2 type schema 1986, and a Res2 type schema 1996. Proc1 1924 and Proc2 1964 may be converted, respectively, into human-readable documentations 1944 and 1984.

Fourth example pseudocode for a plum table associated with the technology is given below, wherein the owner signature has been validated.

PlumIDValue_1 Timestamp1 text/plain Plum1 Content Preview: Content_1
PlumIDValue_2 Timestamp2 text/plain Plum2 Content Preview: Content_2
PlumIDValue_3 Timestamp3 text/plain Plum3 Content Preview: Content_3
PlumIDValue_4 Timestamp4 text/plain Plum4 Content Preview: Content_4
PlumIDValue_5 Timestamp5 text/plain Plum5 Content Preview: Content_5
PlumIDValue_6 Timestamp6 BranchNode json Plum6 Content Preview: Branch Root
PlumIDValue_7 Timestamp7 BranchNode json Plum7 Content Preview: Initial statement
PlumIDValue_8 Timestamp8 BranchNode json Plum8 Content Preview: Revised statement
PlumIDValue_9 Timestamp9 text/plain Plum9 Content Preview: Content_9
PlumIDValue_10 Timestamp10 text/plain Plum10 Content Preview: Content_10
PlumIDValue_11 Timestamp11 text/plain Plum11 Content Preview: Content_11
PlumIDValue_12 Timestamp12 text/plain Plum12 Content Preview: Content_12
PlumIDValue_13 Timestamp13 OwnedData json Plum13 Content Preview: OwnerVerifiedSig13
PlumIDValue_14 Timestamp14 PlumSig json Plum14 Content Preview: OwnerVerifiedSig13
PlumIDValue_15 Timestamp15 OwnedData json Plum15 Content Preview: OwnerVerifiedSig15
PlumIDValue_16 Timestamp16 PlumSig json Plum16 Content Preview: OwnerVerifiedSig15
PlumIDValue_17 Timestamp17 OwnedData json Plum17 Content Preview: OwnerVerifiedSig17
PlumIDValue_18 Timestamp18 PlumSig json Plum18 Content Preview: OwnerVerifiedSig18

Computer System

Figure 20:
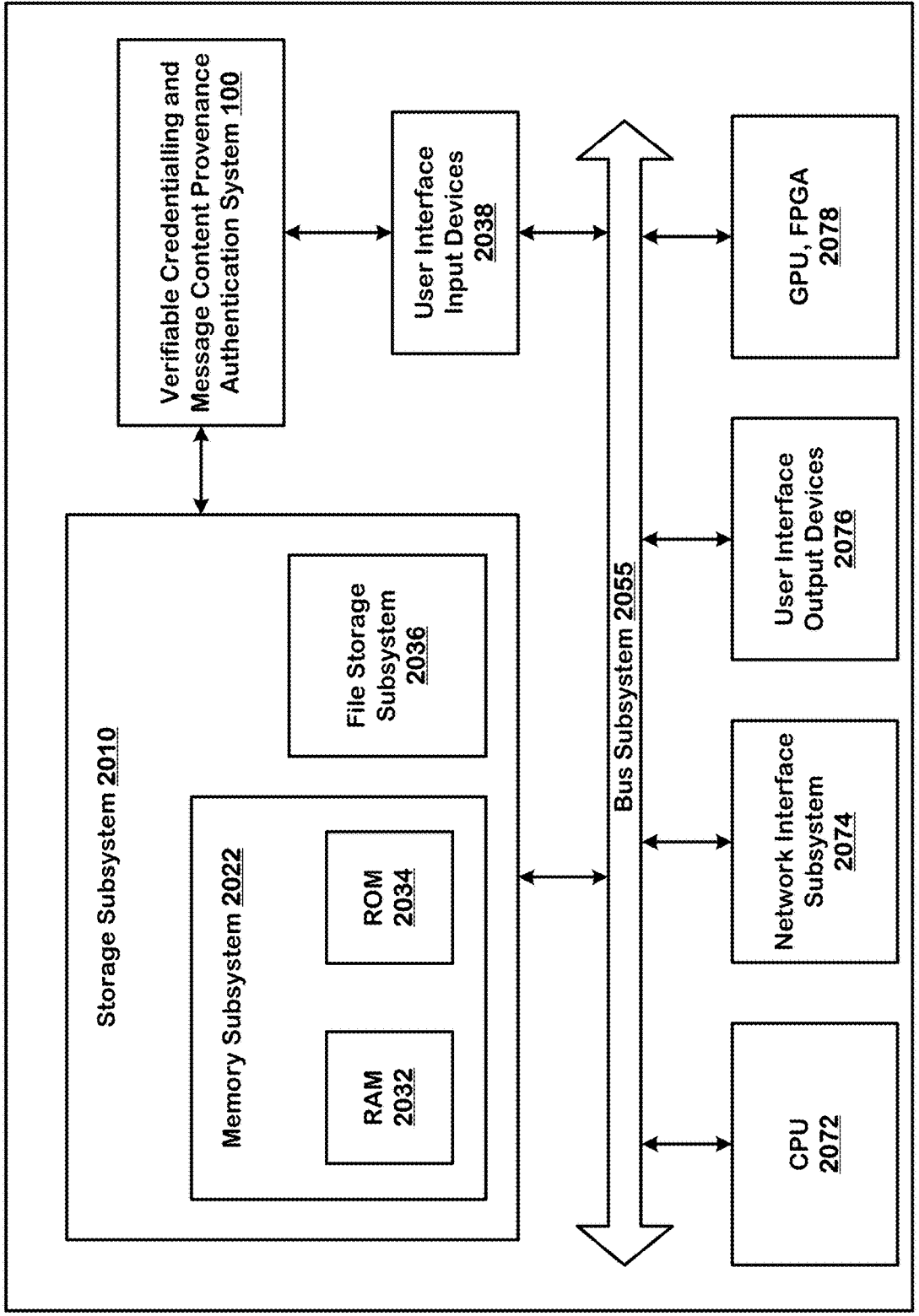
FIG. 20 is a simplified block diagram of a computer system that can be used for the technology disclosed, within accordance with an implementation of the disclosed technology.

FIG. 20 is a simplified block diagram of a computer system 2000 that can be used for generating a graphical summary of a meeting that provides a reflection of a group's conversation in a tapestry, within accordance with an implementation of the disclosed technology. Computer system 2000 includes at least one central processing unit (CPU) 2072 that communicates with a number of peripheral devices via bus subsystem 2055 and system 100. These peripheral devices can include a storage subsystem 2010 including, for example, memory devices and a file storage subsystem 2036, user interface input devices 2037, user interface output devices 2076, and a network interface subsystem 2074. The input and output devices allow user interaction with computer system 2000. Network interface subsystem 2074 provides an interface to outside networks, including an interface to corresponding interface devices in other computer systems.

In one implementation, system 100 is communicably linked to the storage subsystem x10 and the user interface input devices 2037.

User interface input devices 2037 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2000.

User interface output devices 2076 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2000 to the user or to another machine or computer system.

Storage subsystem 2010 stores programming and data constructs that provide the functionality of some or all of the modules and methods described. Subsystem 2077 can be graphics processing units (GPUs) or field-programmable gate arrays (FPGAs).

Memory subsystem 2022 used in the storage subsystem 2010 can include a number of memories including a main random access memory (RAM) 2032 for storage of instructions and data during program execution and a read only memory (ROM) 2034 in which fixed instructions are stored. A file storage subsystem 2036 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2036 in the storage subsystem 2010, or in other machines accessible by the processor.

Bus subsystem 2055 provides a mechanism for letting the various components and subsystems of computer system 2000 communicate with each other as intended. Although bus subsystem 2055 is shown schematically as a single bus, alternative implementations of the bus subsystem can use multiple busses.

Computer system 2000 itself can be of varying types including a personal computer, a portable computer, a workstation, a computer terminal, a network computer, a television, a mainframe, a server farm, a widely-distributed set of loosely networked computers, or any other data processing system or user device. Due to the everchanging nature of computers and networks, the description of computer system 2000 depicted in FIG. 20 is intended only as a specific example for purposes of illustrating the preferred embodiments of the present invention. Many other configurations of computer system 2000 are possible having more or less components than the computer system depicted in FIG. 20.

PARTICULAR IMPLEMENTATIONS

Some particular implementations and features for the technology disclosed are described in the following discussion.

In one disclosed implementation, the system is configured to bidirectionally authenticating two-way messaging between users using verifiable credentials at multiple secure web endpoints. The system comprises a user credentialing administration logic configured to provide a verifiable presentation of a received credential received from a user or a trusted identity authenticator on behalf of the user, either for a user (i) seeking to send a message originating at a first digital endpoint, or (ii) seeking to receive a message at a second digital endpoint. The verifiable presentation can include an electronic presentation of one or more instances of electronic evidence (a) personally identifying the user and (b) supporting any credentialing issued to the user, or (c) a claim that the user is indeed associated with a digital endpoint from which the message originates for a sender user or to which the message is sent for a recipient user. The system also comprises a message exchange logic that is configured to generate a link containing query parameters uniquely identifying the message for a message being sent on behalf of a sender user. The link can include, for example, (x) a decentralized identifier (DID) of the sender user, (y) a universally unique identifier (UUID) of the verifiable presentation, and (z) an authentication information. The message exchange logic is also configured to send a combination of (a) the link, (b) the verifiable presentation, and (c) the message to a digital endpoint identified by the sender user to receive the message (i.e., sending an email to the Recipient's email address). The message exchange logic is also configured to verify the verifiable presentation when receiving a message on behalf of a recipient user and if verifiable, provide the link to the recipient user. In certain implementations, the web portal delegates access to the user credentialing administration logic and verifiable credential of the recipient, while in other implementations, the verifiable presentation for the recipient is generated separately and pasted into the web portal.

In some implementations, the authentication information included in the link comprises a reference to a hash-addressable, hash-verifiable chained data structure ("plum") resident in a data cache and storing content provenance for the message. Each plum comprises a head and a head seal comprising a hash value of the head, metadata and a metadata seal comprising a hash value of the metadata, one or more relations and a relations seal comprising a hash value of the relations, and a body and a body seal comprising a hash value of the body. For each message version created and signed using a verified signature of the sender user, a new plum is added to the data cache and chained to an ancestor of a prior message version forming a chain of plums. The verified signature can include the verifiable presentation of the user, obtained by the user credentialing administration logic, and can also include the decentralized identifier of the user. In one implementation, the plum further maintains a time stamp for each validation of a verified signature.

In one disclosed implementation, the message exchange logic is further configured to prompt the sender user for their verified signature and message content when sending the message on behalf of the sender user, instantiate a plum, incorporate the message content and the digital identifier of the sender user into the body, compute a body seal hash of the body, compute a head seal hash value for the plum and add the plum to the data cache.

In another disclosed implementation, the system includes the message exchange logic iterating through the chain of plums until a plum(s) corresponding to a message version(s) whose content provenance is to be authenticated is/are reached.

In yet another disclosed implementation, when adding a new version of a message, the message exchange logic is configured to instantiate a child plum, populate the body with new version message content and verified signature of the sender user, incorporate relation information of the plum as a parent plum, compute a body seal hash of the body, a relations seal hash value of the relation information, and a head seal hash value for the child plum and add the child plum to the data cache.

The system described in this section and other sections of the technology disclosed can include one or more of the following features and/or features described in connection with additional system disclosed. In the interest of conciseness, the combinations of features disclosed in this application are not individually enumerated and are not repeated with each base set of features. The reader will understand how features identified in this method can readily be combined with sets of base features identified as implementations.

Some implementations of the disclosed system further include the message exchange logic authenticating content provenance of a message on behalf of a recipient user. In authenticating the content provenance of a message on behalf of the recipient user, the message exchange logic is configured to iterate through the chain of plums beginning with an ancestral plum and until a plum(s) corresponding to a message version(s) whose content provenance is to be authenticated is/are reached, and for each plum in the chain of plums, verify matching corresponding data entries for (a) a nonce, (b) a subject, (c) ancestral relationship, and (d) a verified signature, and verify concordance with other plums in the chain of plums of owned data for the plum including: (x) the decentralized identifier, (y) additional metadata, and (z) previous owned data. Other implementations of the disclosed system further include tracking, by each corresponding plum, a difference between metadata and content of a subsequent version and metadata and content of a previous version.

In some implementations, the message exchange logic is embodied by a server, and neither the user seeking to send a message nor the user seeking to validate a received message need to establish an account on the server. Certain implementations can include the message exchange logic further maintaining at least one of a whitelist and a blacklist for users. Other implementations may include the message exchange logic further maintaining at least one of a whitelist and a blacklist for credential types. However, these implementations are explicitly listed for convenience of description and should not be considered limitations of the implementations of the technology disclosed.

Other implementations of the systems described in this section can include a tangible non-transitory computer-readable storage medium storing program instructions loaded into memory that, when executed on processors cause the processors to perform any of the methods described above. Yet another implementation of the systems described in this section can include a device including memory and one or more processors operable to execute computer instructions, stored in the memory, to perform any of the methods described above.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method of providing a verifiable presentation of a received credential received from a user or a trusted identity authenticator on behalf of the user, either for a user (i) seeking to send a message originating at a first digital endpoint, or (ii) seeking to receive a message at a second digital endpoint. The verifiable presentation can include an electronic presentation of one or more instances of electronic evidence (a) personally identifying the user and (b) supporting any credentialing issued to the user, or (c) a claim that the user is indeed associated with a digital endpoint from which the message originates for a sender user or to which the message is sent for a recipient user. The method also comprises generating a link containing query parameters uniquely identifying the message for a message being sent on behalf of a sender user. The link can include, for example, (x) a decentralized identifier (DID) of the sender user, (y) a universally unique identifier (UUID) of the verifiable presentation, and (z) an authentication information. The method also comprises sending a combination of (a) the link, (b) the verifiable presentation, and (c) the message to a digital endpoint identified by the sender user to receive the message (i.e., sending an email to the Recipient's email address) and verifying the verifiable presentation when receiving a message on behalf of a recipient user and if verifiable, provide the link to the recipient user. In one implementation of the technology disclosed, the verifiable presentation is logged for future auditability when the link is sent.

In addition to auditing verifiable presentations, the technology disclosed can also employ artificial intelligence or machine learning algorithms to securely detect fraudulent use of verifiable credentials by observing patterns in the messages signed by them. These predictions may take the form of risk scores, which may be visible to the message sender or recipient. The risk scores may also factor in the time difference between when the verifiable presentation of a verifiable credential was issued, and the time the link was opened or otherwise processed.

Implementations of the disclosed technology may include one or more of the following features. The disclosed methods may include leveraging user cryptographic wallets storing verifiable credentials on behalf of one or more of the sender user and the recipient user. In many implementations, the sender user and recipient user have no prior knowledge of each other. In some implementations, the user verifiable credentials are not tied to self-sovereign identities. Protocols that rely on self-sovereign identities, such as DIDComm, are not adopted and integrated into many production systems. Hence, some implementations of the technology disclosed combine verifiable credentials with legacy channels to support and the features disclosed herein can be similarly combined with an enterprise's digital identity management system independent of whether or not the user credentials are self-sovereign. Accordingly, some implementations of the technology disclosed involve leveraging of verifiable credentials that are not adherent to W3C protocol. Certain implementations of the technology disclosed involve leveraging digital identities within ZKP systems, while other implementations involve leveraging digital identities that do not adhere to ZKP. One implementation of the technology disclosed leverages a KERI microledger, while other implementations do not.

One implementation involves partially obscured verifiable credentials of users. Another implementation involves fractional verifiable credentials of users. Certain implementations of the technology disclosed adhere to LEI. Other implementations of the technology disclosed adhere to GLEIF. Many implementations of the technology disclosed employ an ad hoc approach that enables combining verifiable credentials with an enterprise's legacy channels to support.

One general aspect includes a tangible non-transitory computer-readable storage media. The tangible non-transitory computer-readable storage media can include a program with instructions to perform a method of providing a verifiable presentation of a received credential received from a user or a trusted identity authenticator on behalf of the user, either for a user (i) seeking to send a message originating at a first digital endpoint, or (ii) seeking to receive a message at a second digital endpoint. The verifiable presentation can include an electronic presentation of one or more instances of electronic evidence (a) personally identifying the user and (b) supporting any credentialing issued to the user, or (c) a claim that the user is indeed associated with a digital endpoint from which the message originates for a sender user or to which the message is sent for a recipient user. The method also comprises generating a link containing query parameters uniquely identifying the message for a message being sent on behalf of a sender user. The link can include, for example, (x) a decentralized identifier (DID) of the sender user, (y) a universally unique identifier (UUID) of the verifiable presentation, and (z) an authentication information. The method also comprises sending a combination of (a) the link, (b) the verifiable presentation, and (c) the message to a digital endpoint identified by the sender user to receive the message (i.e., sending an email to the Recipient's email address) and verifying the verifiable presentation when receiving a message on behalf of a recipient user and if verifiable, provide the link to the recipient user. Other embodiments of this aspect include corresponding computer systems, apparatus, and computer programs recorded on one or more computer storage devices, each configured to perform the actions of the methods.

Implementations of the described techniques may include hardware, a method or process, or computer software on a computer-accessible medium.

Another disclosed system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One implementation of the technology disclosed includes a computer-implemented method of bidirectional authentication between two users leveraging a messaging platform, wherein the method includes a web portal that presents a form for gathering information from a recipient user, i.e., information requested by the sender user in a message sent via the messaging platform. The information gathered from the recipient user within the form can be sent to the sender user in a response message.

In many implementations of the technology disclosed, sending an email to the recipient sender as a "carbon copy" of information entered into the form.

Some implementations include sharing the Verifiable Presentation for purposes of authentication, changing the method of integrating the Verifiable Presentation with the message and/or using a standard that is similar to a Verifiable Credential, but not exactly the same (e.g., a more general or different cryptographic proof of identity), to enable compatibility with an enterprise's legacy channel(s). Implementations of the described techniques may include hardware, a method or process, or computer software on a computer-accessible medium.

The disclosed technology, in certain implementations, includes the computer-implemented method of employing artificial intelligence or machine learning algorithms to securely detect fraudulent use of verifiable credentials by observing patterns in the messages signed by them. These predictions may take the form of risk scores, which may be visible to the message sender or recipient. The risk scores may also factor in the time difference between when the verifiable presentation of a verifiable credential was issued, and the time the link was opened or otherwise processed.

Any data structures and code described or referenced above are stored according to many implementations on a computer readable storage medium, which may be any device or medium that can store code and/or data for use by a computer system. This includes, but is not limited to, volatile memory, non-volatile memory, application-specific integrated circuits (ASICs), field-programmable gate arrays (FPGAs), magnetic and optical storage devices such as disk drives, magnetic tape, CDs (compact discs), DVDs (digital versatile discs or digital video discs), or other media capable of storing computer-readable media now known or later developed.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein. The scope of the technology disclosed is defined by the appended claims.

What is claimed is:

1. A system comprising one or more hardware processors coupled to memory storing instructions for bidirectional authenticated two-way messaging between users using verifiable credentials at multiple secure web endpoints, which instructions when executed by the one or more hardware processors implement:

a user credentialing administration logic, configured to:
        provide a verifiable presentation of a received credential received from a user or a trusted identity authenticator on behalf of the user, the verifiable presentation including an electronic presentation of one or more instances of electronic evidence (a) personally identifying the user and (b) supporting any credentialing issued to the user, or (c) a claim that the user is indeed associated with a digital endpoint from which a message originates for a sender user or to which the message is sent for a recipient user,
        wherein the user is seeking to send the message originating at a first digital endpoint, or
        seeking to receive the message at a second digital endpoint; and
    a message exchange logic, configured to:
        (i) for sending a message on behalf of a sender user seeking to send the message, generate a link containing query parameters uniquely identifying the message, including (x) a decentralized identifier (DID) of the sender user, (y) a universally unique identifier (UUID) of the verifiable presentation, and (z) an authentication information, and send to a digital endpoint identified by the sender user to receive the message, a combination of (a) the link, (b) the verifiable presentation, and (c) the message; and (ii) for receiving a message on behalf of a recipient user seeking to receive the message, verify the verifiable presentation and if verifiable, provide the link to the recipient user, the link directing the recipient user to a web portal to receive a recipient verifiable presentation from or on behalf of the recipient user, and if verifiable, provide the recipient user with access to the message, and notify the sender user with a response message; thereby providing interoperable and bidirectional authentication of sender user identity and recipient user identity, without need for either user to create an account with the message exchange logic.

2. The system of claim 1, wherein the authentication information comprises a reference to a hash-addressable, hash-verifiable chained data structure ("plum") resident in a data cache and storing content provenance for the message, each plum comprising:

a head and a head seal comprising a hash value of the head, metadata and a metadata seal comprising a hash value of the metadata, one or more relations and a relations seal comprising a hash value of the relations, and a body and a body seal comprising a hash value of the body, and wherein for each message version created and signed using a verified signature of the sender user, a new plum is added to the data cache and chained to an ancestor of a prior message version forming a chain of plums.

3. The system of claim 2, wherein the message exchange logic is further configured to iterate through the chain of plums until a plum(s) corresponding to a message version(s) whose content provenance is to be authenticated is/are reached.

4. The system of claim 2, wherein the message exchange logic is further configured to:

for sending a message on behalf of a sender user seeking to send a message, prompt the sender user for their verified signature and message content, instantiate a plum, incorporate the message content and the digital identifier of the sender user into the body, compute a body seal hash of the body, compute a head seal hash value for the plum and add the plum to the data cache.

5. The system of claim 4, wherein of the message exchange logic is further configured to:

for adding a new version of the message, instantiate a child plum, populate the body with new version message content and verified signature of the sender user, incorporate relation information of the plum as a parent plum, compute a body seal hash of the body, a relations seal hash value of the relation information, and a head seal hash value for the child plum and add the child plum to the data cache.

6. The system of claim 2, wherein the message exchange logic is further configured to:

for authenticating content provenance of a message on behalf of a recipient user, iterate through the chain of plums beginning with an ancestral plum and until a plum(s) corresponding to a message version(s) whose content provenance is to be authenticated is/are reached, and for each plum in the chain of plums verify matching corresponding data entries for (a) a nonce, (b) a subject, (c) ancestral relationship, and (d) a verified signature, and verify concordance with other plums in the chain of plums of owned data for the plum including: (x) the decentralized identifier, (y) additional metadata, and (z) previous owned data.

7. The system of claim 2, wherein the verified signature includes a verifiable presentation obtained by the user credentialing administration logic.

8. The system of claim 2, wherein the verified signature includes the decentralized identifier of the user.

9. The system of claim 2, wherein for each subsequent version, tracking by each corresponding plum, a difference between metadata and content of that version and metadata and content of a previous version.

10. The system of claim 2, further including the plum maintaining a time stamp for each validation of a verified signature.

11. The system of claim 1, wherein the message exchange logic is embodied by a server; and wherein neither the user seeking to send a message nor the user seeking to validate a received message need to establish an account on the server.

12. The system of claim 1, wherein the message exchange logic further maintains at least one of a whitelist and a blacklist for users.

13. The system of claim 1, wherein the message exchange logic further maintains at least one of a whitelist and a blacklist of credential types.

14. The system of claim 1, wherein the user credentialing administration logic further logs the verifiable presentation for future auditability when the link is sent.

15. The system of claim 1, wherein the verifiable presentation for the recipient user is generated separately and pasted into the web portal.

16. The system of claim 1, wherein the web portal delegates access to the user credentialing administration logic and verifiable credential of the recipient user.

17. The system of claim 1, further including a cryptographic wallet storing verifiable credentials on behalf of one or more of the sender user and the recipient user.

18. The system of claim 1, wherein the sender user and the recipient user have no prior knowledge of each other.

19. The system of claim 1, further including the web portal presenting a form for gathering from the recipient user, information requested by the sender user in the message, and sending information as gathered from the recipient user to the sender user in the response message.

20. The system of claim 19, further including sending an email to the recipient sender as a "carbon copy" of information entered into the form.

21. The system of claim 1, wherein the verifiable credential (VC) includes a VC type selected from of a set of VC types including a self-sovereign or an entity-sovereign, a World Wide Web Consortium (w3c) adherent, a Zero-Knowledge Proof (ZKP), a Key Event Receipt Infrastructure (KERI) microledger based, a partially obscured or a fractional VC and a Legal Entity Identifier (LEI) or a Global Legal Entity Identifier (GLEIF) adherent.

* * * * *